(12) United States Patent
Ding

(10) Patent No.: US 12,049,475 B2
(45) Date of Patent: Jul. 30, 2024

(54) BISPHOSPHONATE DRUG CONJUGATES

(71) Applicant: BRISE PHARMACEUTICALS CO., LTD., Shanghai (CN)

(72) Inventor: Qiang Ding, Guangdong (CN)

(73) Assignee: BRISE PHARMACEUTICALS CO., LTD., Shanghai (CN)

(*) Notice: Subject to any disclaimer, the term of this patent is extended or adjusted under 35 U.S.C. 154(b) by 638 days.

(21) Appl. No.: 17/269,908

(22) PCT Filed: Jul. 23, 2018

(86) PCT No.: PCT/CN2018/096616
§ 371 (c)(1),
(2) Date: Feb. 19, 2021

(87) PCT Pub. No.: WO2020/019108
PCT Pub. Date: Jan. 30, 2020

(65) Prior Publication Data
US 2021/0309679 A1    Oct. 7, 2021

(51) Int. Cl.
*C07F 9/6561* (2006.01)
*A61K 47/54* (2017.01)
*A61P 19/02* (2006.01)

(52) U.S. Cl.
CPC ......... *C07F 9/6561* (2013.01); *A61K 47/548* (2017.08); *A61P 19/02* (2018.01)

(58) Field of Classification Search
None
See application file for complete search history.

(56) References Cited

FOREIGN PATENT DOCUMENTS

| | | | |
|---|---|---|---|
| CN | 108289964 | 7/2018 | |
| DE | 3203307 | 7/1983 | |
| WO | 02094833 | 11/2002 | |
| WO | WO-02094833 A1 * | 11/2002 | ........... C07D 471/04 |
| WO | 2004048381 | 6/2004 | |
| WO | 2004048382 | 6/2004 | |
| WO | 2015028850 | 3/2015 | |
| WO | 2015155753 | 10/2015 | |
| WO | WO-2015168636 A1 * | 11/2015 | ............. A61K 35/32 |

OTHER PUBLICATIONS

Rothman et al., "The use of common genetic polymorphisms to enhance the epidemiologic study of environmental carcinogens", 2000, Biochimica et Biophysica Acta, 1471, C1-C10 (Year: 2000).*
Allen et al., "Future therapies for cystic fibrosis", 2023, Nature Communications, 14, pp. 1-13 (Year: 2023).*
Cayci et al., "Osteoarthritis of the wrist", 2014, Plastic and Reconstructive Surgery, 133, pp. 605-615 (Year: 2014).*
University of Rochester, "How to Help Prevent Osteoarthritis", 2023, pp. 1-4 (Year: 2023).*
Huang et al., "Recent progress in TGF-beta inhibitors for cancer therapy", 2021, Biomedicine & Pharmacotherapy, 134, pp. 1-10 (Year: 2021).*
Park et al., "TGF-beta Inhibitors for Therapeutic Management of Kidney Fibrosis", 2022, Pharmaceuticals, pp. 1-17 (Year: 2022).*
American Lung Association, "7 Things Everyone Should Known about Pulmonary Fibrosis", 2023, pp. 1-7 (Year: 2023).*
Van der Kraan, "Inhibition of transforming growth factor-β in osteoarthritis. Discrepancy with reduced TGFB signaling in normal joints ", 2022, Osteoarthritis and Cartilage Open, 4, pp. 1-6 (Year: 2022).*
Van Hul et al., "Camurati-Engelmann Disease", 2019, Calcified Tissue International, 104, pp. 554-560 (Year: 2019).*
Wan et al., "Effect of transforming growth factor beta (TGF-beta) receptor I kinase inhibitor on prostate cancer bone growth", 2012, Bone, 50, pp. 695-703 (Year: 2012).*
Xing et al., "Bisphosphonates therapy for osteoarthritis: a meta-analysis of randomized controlled trials", 2016, SpringerPlus, 5, pp. 1-8 (Year: 2016).*

* cited by examiner

*Primary Examiner* — Jeffrey H Murray
*Assistant Examiner* — Madeline E Braun
(74) *Attorney, Agent, or Firm* — NIXON & VANDERHYE, PC

(57) ABSTRACT

Provided herein are novel conjugates of TGF-beta inhibitors and bisphosphonates, pharmaceutical compositions comprising the conjugates, methods of preparing the conjugates, and methods of using the conjugates, for example, for the treatment of a bone disease or disorder, such as osteoarthritis.

30 Claims, 6 Drawing Sheets

BISPHOSPHONATE DRUG CONJUGATES

BACKGROUND OF THE INVENTION

Field of the Invention

Figure 1:
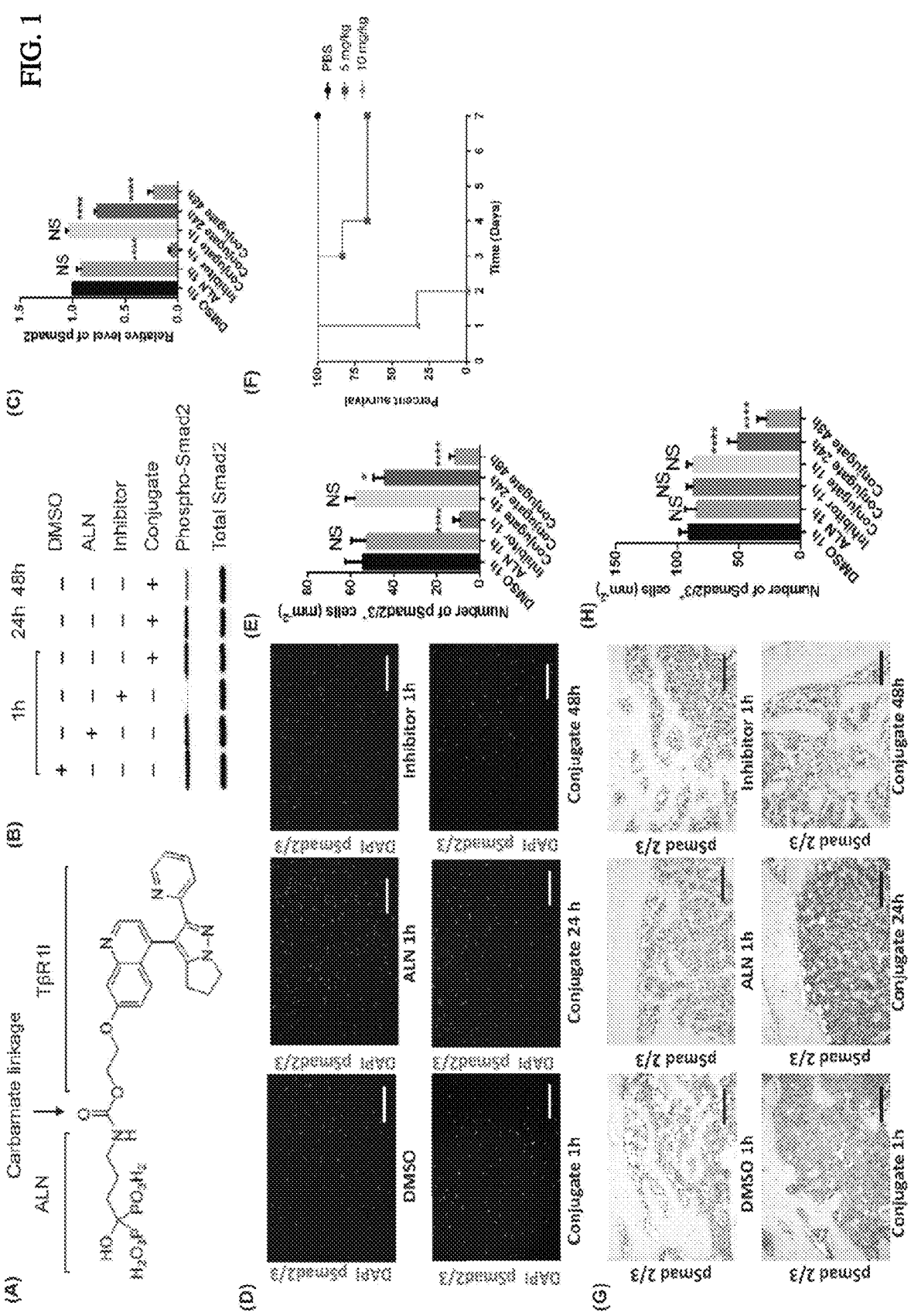

In various embodiments, the present invention generally relates to a novel class of conjugates of transforming growth factor (TGF) beta inhibitors and bisphosphonates, pharmaceutical compositions, methods of preparing the conjugates, and methods of using the conjugates.

Background Art

Transforming growth factor-beta (TGF-β) is a prototype for a large family of growth and differentiation factors that regulate development. TGF-β family members activate transmembrane serine/threonine receptor kinases, thereby initiating a signaling cascade via Smads, a class of intracellular signaling effectors that regulate gene expression. TGF-β is a potent inducer of growth arrest in many cell types, including epithelial cells. This activity is the basis of the tumor suppressor role of the TGF-β signaling system in carcinomas. Other activities, including TGF-β-induced epithelial-to-mesenchymal differentiation, contribute to cancer progression. TGF-β family signaling is of special relevance in mesenchymal differentiation, including bone development. Deregulated expression or activation of components of this signaling system can contribute to skeletal diseases, e.g. osteoarthritis. See Wakefield, et al. (2002) Current Opinion in Genetics & Development 12:22-29; Siegel, et al. (2003) Nature Reviews (Cancer) 3:807-820; Dumont, et al. (2003) Cancer Cell 3:531-536.

Camurati-Engelmann disease (CED) is a chromosomal dominant genetic disorder. It is caused by the mutations in the chromosomal region 19q13 that encodes the latency-associated peptide (LAP) of transforming growth factor-β1 (TGF-β1), a coupling factor for bone resorption and formation during remodeling. The mutations in the LAP cause TGF-β1 activation upon secretion in bone marrow, which disrupts bone resorption from formation. CED commonly manifests between childhood and 30 years of age, often presenting as cortical bone thickening in the long bone. About 98% of patients show typical long bone dysplasia, while 54% and 63% show deformities in the skull and pelvis, respectively. Though the etiology of CED is known, there are no effective treatments that control CED-associated bone dysplasia. Glucocorticoids are currently the most common therapies to treat CED patients; however, these drugs only relieve bone pain and fatigue and do not effectively attenuate or control CED progression.

It was known that excessive active TGF-β1 can induce aberrant bone remodeling to drive CED progression. Normally, TGF-β1 is released from the bone matrix during bone resorption and activated by osteoclasts. The activated TGF-β1 guides bone marrow mesenchymal stem cells (BMSCs) to migrate to the bone resorption sites for new bone formation. In CED, TGF-β1 is directly activated upon secretion. The high level of active TGF-β1 in bone marrow disrupts the normal TGF-β1 gradient and uncouples bone resorption from formation. By systemically injecting a TGF-β type 1 receptor inhibitor (TβR1I), bone morphology and uncoupled bone remodeling in the CED mouse model can be rescued. However, systemic treatment of TβR1I might cause serious side effects because TGF-β1 receptors are widely expressed and broadly affect many other functions, such as immune response and angiogenesis. Thus, delivering TβR1I specifically to bone can significantly reduce its side effects and increase efficacy in clinical uses.

TGF-β1 was known to instruct BMSCs migration and regulate local angiogenesis but had no influence on osteogenesis. Aberrant bone and vessel formation are typical phenotypes in CED mice, indicating TGF-β1 may indirectly regulate osteogenesis through angiogenesis. A newly discovered type of CD31 and Endomucin double positive (CD31+Emcn+) vessel was reported to link osteogenesis with angiogenesis. The vessel provided a pro-osteogenic differentiation microenvironment and was surrounded by BMSCs. Leptin receptor positive (LepR+) BMSCs, a subtype of BMSCs contributing to the most bone formation in adult mice, were perivascularly distributed. These cells could differentiate into osteoblastic, chondrogenic, or adipogenic cells according to the local microenvironment. These studies suggest TGF-β1 may regulates osteogenesis via CD31+Emcn+ vessel mediated LepR+BMSCs osteogenic differentiation.

Osteoarthritis is the most common degenerative joint disorder, mainly afflicting the weight-bearing joints, like hips and knees, and is the leading cause of physical disability, predicted to affect 67 million people in the United States by 2030. Despite the identified risk factors, e.g. mechanical, metabolic or genetic, the exact pathogenesis of osteoarthritis remains unclear. Currently, there is no effective disease modifying treatment for osteoarthritis until the end stage of disease necessitating joint replacement.

Articular cartilage degeneration is the primary concern in osteoarthritis, which has recently been attributed to hypoxia-inducible factor-2α (HIF-2α) and complement component 5 (C5), in addition to the well established ADAMTS5 and matrix metalloproteinase 13 (MMP13). Homeostasis and integrity of articular cartilage rely on its biochemical and biomechanical interplay with subchondral bone and other joint tissues. Subchondral bone provides the mechanical support for overlying articular cartilage during the movement of joints and undergoes constant adaptation in response to changes in the mechanical environment through modeling or remodeling. In the situation of instability of mechanical loading on weight-bearing joints, such as occurs with ligament injury, excessive body weight, or weakening muscles during aging, the subchondral bone and calcified cartilage zone undergo changes. For instance, rupture of anterior cruciate ligament (ACL) increases the risk of knee osteoarthritis, and approximately 20-35% of individuals with osteoarthritis are estimated to have had an incidental ACL tear. Clinically, osteophyte formation, subchondral bone sclerosis, disruption of tidemark accompanied by angiogenesis at the osteochondral junction, and articular cartilage degeneration are characteristics of osteoarthritis. Bone marrow lesions are closely associated with pain and implicated to predict the severity of cartilage damage in osteoarthritis. In healthy articular cartilage, matrix turnover remains at relatively low rates and chondrocytes resist proliferation and terminal differentiation. During progression of osteoarthritis, type X collagen, alkaline phosphatase, Runt-related transcription factor 2 (RUNX2), and MMP13 are expressed in articular chondrocytes with decreased proteoglycans and expanded calcified cartilage zones in articular cartilage. However, the exact mechanism underlying the potential contributions of subchondral bone to articular cartilage degeneration during osteoarthritis progression is largely unknown.

The role of TGF-β in the pathogenesis of osteoarthritis has drawn more and more attention in recent years. TGF-β is essential for maintenance of articular cartilage metabolic homeostasis and structural integrity. TGF-β1 stimulates chondrocyte proliferation, and knockout of TGF-β1 or interruption of TGF-β signaling in the articular cartilage results in loss of proteoglycans and cartilage degeneration in mice. The elevated ALK1-Smad1/5 vs. ALK5-Smad2/3 ratio in articular cartilage might contribute to pathogenesis of osteoarthritis. It has been demonstrated that ablation of endogenous TGF-β1 activity reduces osteophyte formation in vivo but aggravates articular cartilage degeneration in osteoarthritis animal models. It was previously shown that TGF-β1 is activated during osteoclastic bone resorption and induces the migration of bone marrow MSCs to resorption pits for new bone formation serving as a coupling factor. It was also found that inhibition of TGF-β1 activity in the subchondral bone attenuated its pathological changes and reduced degeneration of articular cartilage in different osteoarthritis animal models. Thus, inhibition of transforming growth factor beta (TGF-beta or TGFβ) can be used as a therapy for osteoarthritis. See e.g., U.S. Publication No. 2015/0139909, the content of which is herein incorporated by reference in its entirety.

TGF-β is known for its anabolic effects on articular cartilage homeostasis by stimulating the production of extracellular matrix proteins and preventing terminal differentiation of chondrocytes. As detailed in U.S. Publication No. 2015/0139909, it was found that changes in mechanical loading on the joints increased the number of osteoclasts in the subchondral bone as early as 7 days post surgery in the ACLT animal model. High concentrations of TGF-β1 were activated during osteoclast bone resorption to recruit nestin$^+$ MSCs for the subsequent uncoupled bone formation. Notably, osteoclastic bone resorption was spatiotemporally uncoupled with TGF-β1-induced recruitment of nestin$^+$ MSCs and led to aberrant bone formation, which was further substantiated by development of osteoarthritic-like changes in CED mice. Relative to a single phase of uncoupled sequential bone resorption and formation in the mouse ACLT model, human osteoarthritis appeared more complex with multiple phases. It was also found some areas of the articular cartilage were still intact or in the middle stage of osteoarthritis progression when analyzing specimens from late stage osteoarthritis subjects who underwent knee joint replacement. Consistently, the thickness of the subchondral plate in osteoarthritis specimens is not uniform, although the percent distribution of subchondral plate generally became thicker. Moreover, the concentrations of active TGF-β were higher in subchondral bone with articular cartilage compared that of the healthy controls. The observation suggests that inhibition of TGF-β activity in the subchondral bone may still have therapeutic effects even if individuals with osteoarthritis are not in the early stages. Based on these observations, it was concluded that TGF-β plays a different role in subchondral bone as opposed to its anabolic effect on articular cartilage; the location of the elevated TGF-β1 concentrations in subchondral bone triggers a cascade of events that lead to the development of osteoarthritis. See Id.

Both clinical and animal studies reported that progression of osteoarthritis is accompanied by the accumulation of mesenchymal progenitor cells in joint tissues and synovial fluids. See U.S. Publication No. 2015/0139909. Bone marrow lesions have been identified as a prognostic factor of osteoarthritis progression as it has been found to populate sites of cartilage destruction. It was observed that elevations in TGF-β1 concentrations lead to an increased number of nestin$^+$ MSCs in the subchondral bone marrow in various osteoarthritis animal models. During the normal remodeling process, osteoblasts and their progenitors are primarily observed at the resorption site on the bone surface. However, the altered microenvironment induced by abnormal mechanical loading may lead to "in situ" commitment of osteoprogenitors in the bone marrow cavities. Bone marrow lesions have been characterized as less well mineralized newly formed bone. These clustered bone marrow osteoprogenitors may lead to osteoid islets in the subchondral bone marrow that is visualized as bone marrow lesions under MRI. Moreover, knockout of TGFBR2 in nestin$^+$ MSCs attenuated the development of osteoarthritis in ACLT mice. This result further confirmed that MSCs are the target cells of the aberrant TGF-β signals during osteoarthritis progression. See id. Additionally, bone formation is often coupled with angiogenesis. It is known that the TGF-β signaling pathway in endothelial progenitor cells can promote angiogenesis and TGF-β may stimulate the paracrine machinery in MSCs that further facilitate angiogenesis. Data revealed that blood vessels were increased in the subchondral bone of both ACLT and CED mice in angiography by microphil-perfused experiments. See id. Reduced angiogenesis by inhibition of TGF-β activity may have further attenuated the de novo bone formation in the subchondral bone in the osteoarthritis joints of ACLT mice.

It was further demonstrated that the subchondral bone and articular cartilage act as a functional unit in the joint. See U.S. Publication No. 2015/0139909. In human osteoarthritis joints, the subchondral plates become significantly thicker relative to that of healthy subjects. The subchondral bone was modeled post surgery in ACLT animal models and their thickness dramatically fluctuated. The capacity of chondrocytes to modulate their functional state in response to alterations in mechanical loading is relatively limited compared to the adjacent subchondral bone. Changes in osteochondral junction are therefore proposed to be involved in advancement of the calcified cartilage zone. Data also show that expansion and increased stiffness of subchondral bone changed the distribution of articular cartilage stress. See id. Therefore, TGF-β-induced abnormal bone formation was proposed as contributing to the alteration of the mechanical property of subchondral bone and initiate its expansion causing degeneration of articular cartilage.

In summary, ample evidence supports that inhibition of TGF-beta can be used as a therapy for osteoarthritis, CED, and various other diseases such as those related to bone remodeling.

A number of compounds (for example WO 02/094833, WO 04/048382, WO 04/048381, WO 04/050659, WO 04/021989, WO 04/026871, WO 04/026307) have been identified as TGF-β inhibitors. There still remains a need for compounds or prodrugs that can release compounds that are capable of inhibiting TGF-β signaling.

BRIEF SUMMARY OF THE INVENTION

In various embodiments, the present invention provides novel conjugates of TGF-beta inhibitors and a bisphosphonate, pharmaceutical compositions comprising the conjugates, methods of preparing the conjugates, and methods of using the conjugates, for example, for the treatment of a bone disease or disorder, such as Camurati-Engelmann disease (CED) or osteoarthritis.

In some embodiments, the present disclosure provides a compound of Formula I, or a pharmaceutically acceptable ester thereof, a zwitterion thereof, or a pharmaceutically acceptable salt thereof:

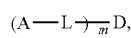

Formula I wherein A, L, m, and D are defined herein. In some embodiments, m is 1. In some embodiments, A is a residue of a bisphosphonate. In some embodiments, L is null or a metabolically cleavable linker. In some embodiments, D is a residue of a TGF-beta inhibitor. In some embodiments, the compound can have a Formula I-1, I-2, I-3, or I-4 as defined herein. In some specific embodiments, the compound can be (1-hydroxy-4-(((2-((4-(2-(pyridin-2-yl)-5,6-dihydro-4H-pyrrolo[1,2-b]pyrazol-3-yl)quinolin-7-yl)oxy)ethoxy)carbonyl)amino)butane-1,1-diyl)bis(phosphonic acid); (1-hydroxy-4-(((4-(2-oxo-2-(2-((4-(2-(pyridin-2-yl)-5,6-dihydro-4H-pyrrolo[1,2-b]pyrazol-3-yl)quinolin-7-yl)oxy)ethoxy)ethyl)phenoxy)carbonyl)amino)butane-1,1-diyl)bis(phosphonic acid); (1-hydroxy-4-(3-(2-((4-(2-(pyridin-2-yl)-5,6-dihydro-4H-pyrrolo[1,2-b]pyrazol-3-yl)quinolin-7-yl)oxy)ethyl)ureido)butane-1,1-diyl)bis(phosphonic acid); (1-hydroxy-4-(4-((4-(2-(pyridin-2-yl)-5,6-dihydro-4H-pyrrolo[1,2-b]pyrazol-3-yl)quinolin-7-yl)oxy)butanamido)butane-1,1-diyl)bis(phosphonic acid); or (1-hydroxy-4-(3-((4-(2-(pyridin-2-yl)-5,6-dihydro-4H-pyrrolo[1,2-b]pyrazol-3-yl)quinolin-7-yl)oxy)propanamido)butane-1,1-diyl)bis(phosphonic acid). In any of the embodiments described herein, the conjugate can exist in the form of a pharmaceutically acceptable ester thereof, or a pharmaceutically acceptable salt, such as a sodium salt.

Certain embodiments of the present disclosure are directed to a pharmaceutical composition comprising a compound of Formula I (e.g., a compound of Formula I-1, I-2, I-3, or I-4, or any of Compounds 1-5) as defined herein, or a pharmaceutically acceptable ester thereof, or a pharmaceutically acceptable salt thereof. The pharmaceutical composition described herein can be formulated for different routes of administration. In some embodiments, the pharmaceutical composition can be formulated for injection or infusion, oral administration, or inhalation.

In some embodiments, the present disclosure also provides a method of delivering a TGF-beta inhibitor to a subject in need thereof. In some embodiments, the method comprises administering to the subject a compound of Formula I (e.g., a compound of Formula I-1, I-2, I-3, or I-4, or any of Compounds 1-5) as defined herein, or a pharmaceutically acceptable ester thereof, or a pharmaceutically acceptable salt thereof, or a pharmaceutical composition comprising the compound or pharmaceutically acceptable ester thereof, or pharmaceutically acceptable salt thereof, as defined herein. In some embodiments, the administering comprises administration via injection or infusion, oral administration, or inhalation. In some embodiments, the administering delivers and/or releases an effective amount of the TGF-beta inhibitor to the bones such as subchondral bones (or vicinity thereof) of the subject.

Certain embodiments of the present disclosure are directed to a method of treating a disease or disorder associated with aberrant TGF-beta activity. In some embodiments, the method comprises administering to the subject in need thereof a therapeutically effective amount of a compound of Formula I (e.g., a compound of Formula I-1, I-2, I-3, or I-4, or any of Compounds 1-5) as defined herein, or a pharmaceutically acceptable ester thereof, or a pharmaceutically acceptable salt thereof, or a pharmaceutical composition comprising the compound or pharmaceutically acceptable ester thereof, or pharmaceutically acceptable salt thereof, as defined herein. In some embodiments, the administering comprises administration via injection or infusion, oral administration, or inhalation. Non-limiting diseases or disorders suitable to be treated with the methods described herein include bone diseases or disorders associated with bone remodeling, such as osteoarthritis or Camurati-Engelmann disease (CED), organ fibrosis, and cancer metastasis (such as bone metastasis).

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

BRIEF DESCRIPTION OF THE DRAWINGS/FIGURES

FIG. 1 presents graphs showing that a conjugate of the present disclosure, Compound 1, delivers a TβR1I specifically to bone and releases it in a time-dependent manner. Specifically, in FIG. 1, Part (A) shows the chemical structure of an ALN-TβR1I conjugate (Compound 1). Part (B) shows the Western-blot analysis of pSmad2 at different time points. Part (C) presents quantification of the Western-blot band intensity in (B). Data are presented as relative level of p-SMAD2/SMAD2 ratio normalized to DMSO condition. Part (D) shows representative pSmad2/3 immunofluorescence staining of cells in culture at different time points. Part (E) presents quantification data of pSmad2/3$^+$ cells in (D). Part (F) shows the 7-day survival rate of wild-type mice that received a conjugate injection (Compound 1) at low to high doses (50 µg/kg, 100 µg/kg, 1 mg/kg, 5 mg/kg, and 10 mg/kg, one intraperitoneal injection per week). All mice treated with 50 µg/kg, 100 µg/kg, or 1 mg/kg survived for 7 days (n=6 per group, not shown). Of 6 mice in the 5 mg/kg group, 2 died in 7 days. Mice treated with 10 mg/kg all died in 3 days. Part (G) shows representative pSmad2/3 immunohistochemistry images (brown cells) of distal tibias from CED mice received 8-week conjugate treatment. Part (H) presents quantification data of pSmad2/3$^+$ cells in (G). In FIG. 1, the following conventions are used: NS, not significant. P<0.01, **P<0.0001 determined by multifactorial ANOVA. All data are reported as the mean±s.d.

Figure 2:
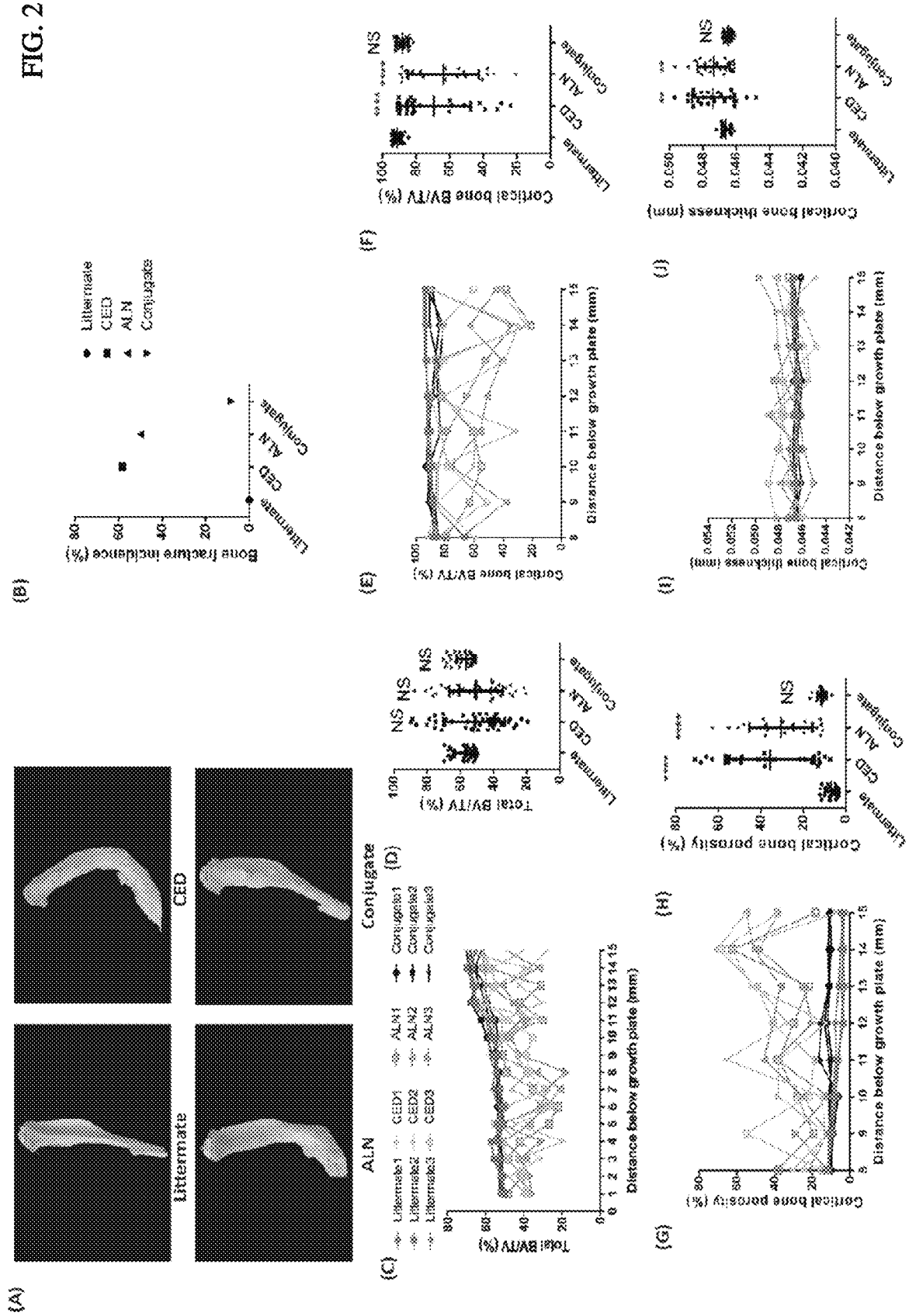

FIG. 2 presents graphs showing that a conjugate of the present disclosure, Compound 1, restored bone parameters after 2-month treatment. Part (A) shows a representative three-dimension reconstruction of whole tibia. Part (B) presents data on bone fracture incidence in each group after 2-month drug treatment (Littermate: 0%; CED: 58.3%; ALN: 50%; Conjugate (Compound 1): 8.3%). Part (C) shows graphs on total BV/TV in tibia cross-sections taken at successive distances from growth plate. Part (D) presents quantification data of Total BV/TV in (C). Part (E) shows cortical BV/TV in cross-sections taken at successive distances from distal one-third of tibia. Part (F) presents quantification data of the cortical BV/TV in (E). Part (G) shows cortical bone porosity in cross-sections taken at successive distances from distal one-third of tibia. Part (H) presents quantification data of the cortical bone porosity in (G). Part (I) shows cross-sections of cortical bone thickness taken at successive distances from distal one-third of tibia.

Part (J) presents quantification data of the cortical bone thickness in (I). n=10. In FIG. 2, the following conventions are used: NS, not significant. P<0.01, **P<0.0001 determined by multifactorial ANOVA. All data are reported as the mean±s.d.

Figure 3:
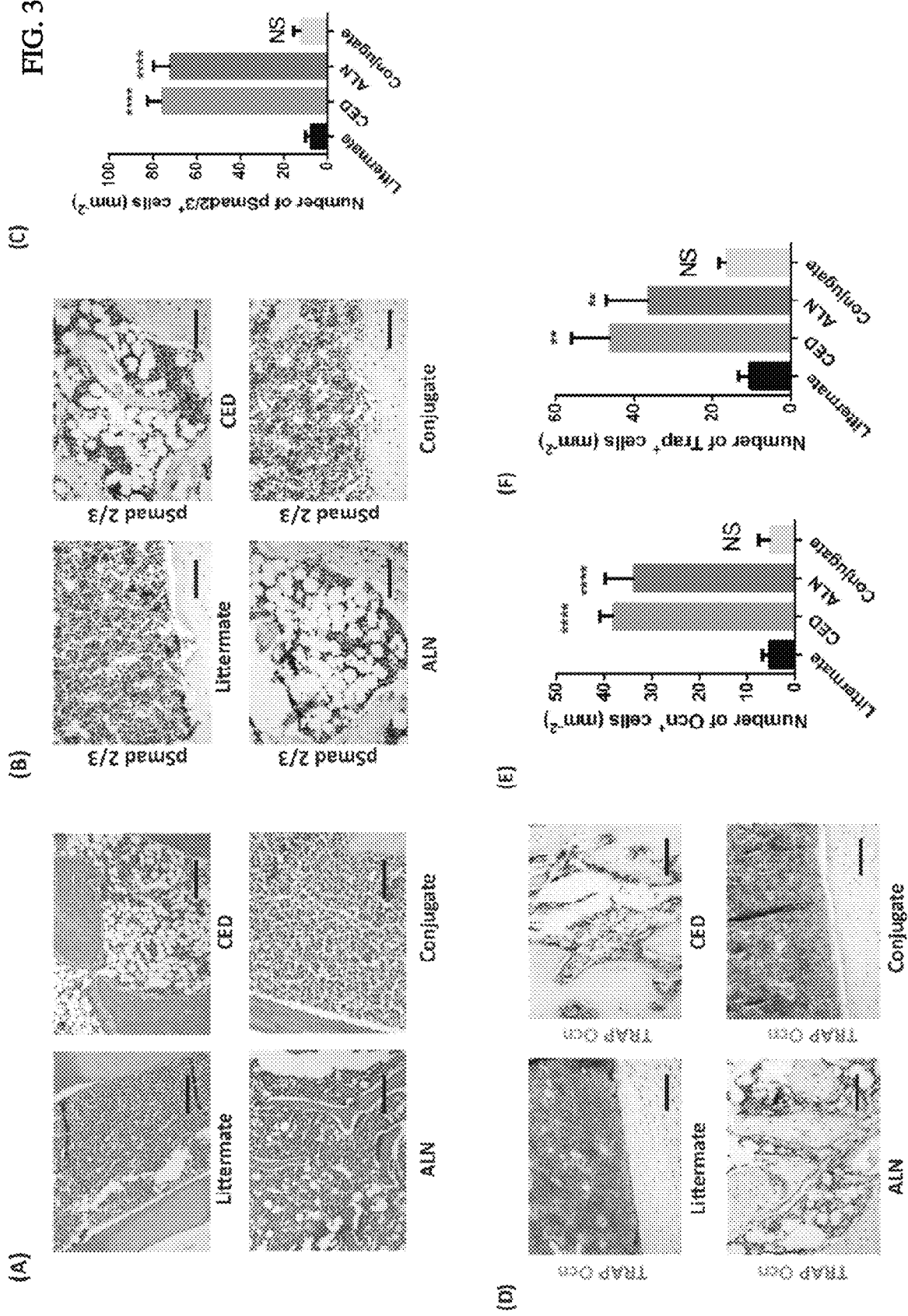

FIG. 3 presents graphs showing that a conjugate of the present disclosure, Compound 1, restored normal bone remodeling after 2-month treatment. Part (A) shows a representative HE staining of distal one-third tibia. Part (B) shows a representative pSmad2/3 immunohistochemistry images (brown cells) from tibia of 3-month-old mice. Part (C) presents quantification data of pSmad2/3$^+$ cells in (B). Part (D) shows tibia sections stained with Ocn antibody for osteoblasts (brown cells) and Trap staining for osteoclasts (purple cells). Part (E) presents quantification data of Ocn$^+$ cells in (E). Part (F) presents quantification data of Trap$^+$ cells in (E). In FIG. 3, the following conventions are used: NS, not significant. P<0.01, **P<0.0001 determined by multifactorial ANOVA. All data are reported as the mean±s.d.

Figure 4:
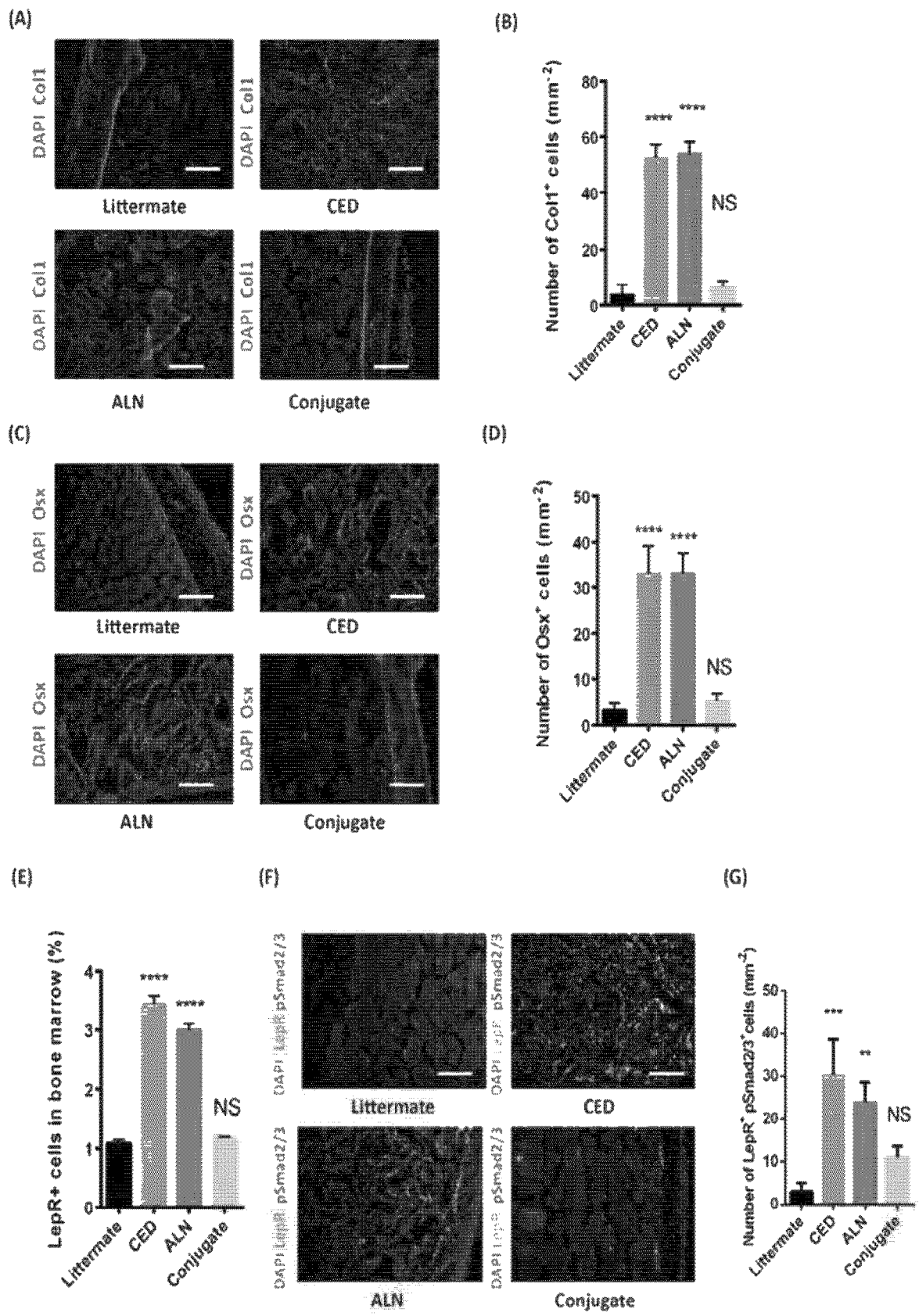

FIG. 4 presents graphs showing that TGF-β recruits LepR$^+$ cells during aberrant bone remodeling. Part (A) shows representative images of Col1$^+$ (red) cells in tibia sections. Part (B) presents quantification data of Col1$^+$ cells in (A). Part (C) shows representative images of Osx$^+$ (red) cells in tibia sections. Part (D) presents quantification data of Osx$^+$ cells in (C). NS, not significant. Part (E) shows flow cytometry analysis for LepR$^+$ cells collected from bone marrow in distal one-third of tibia. Part (F) shows immunofluorescence staining of tibia sections for LepR$^+$ (green) and pSmad2/3$^+$ (red) cells. Part (G) presents quantification data of LepR$^+$pSmad2/3$^+$ cells in (F). In FIG. 4, the following conventions are used: P<0.01, **P<0.0001 determined by multifactorial ANOVA. All data are reported as the mean±s.d.

Figure 5:
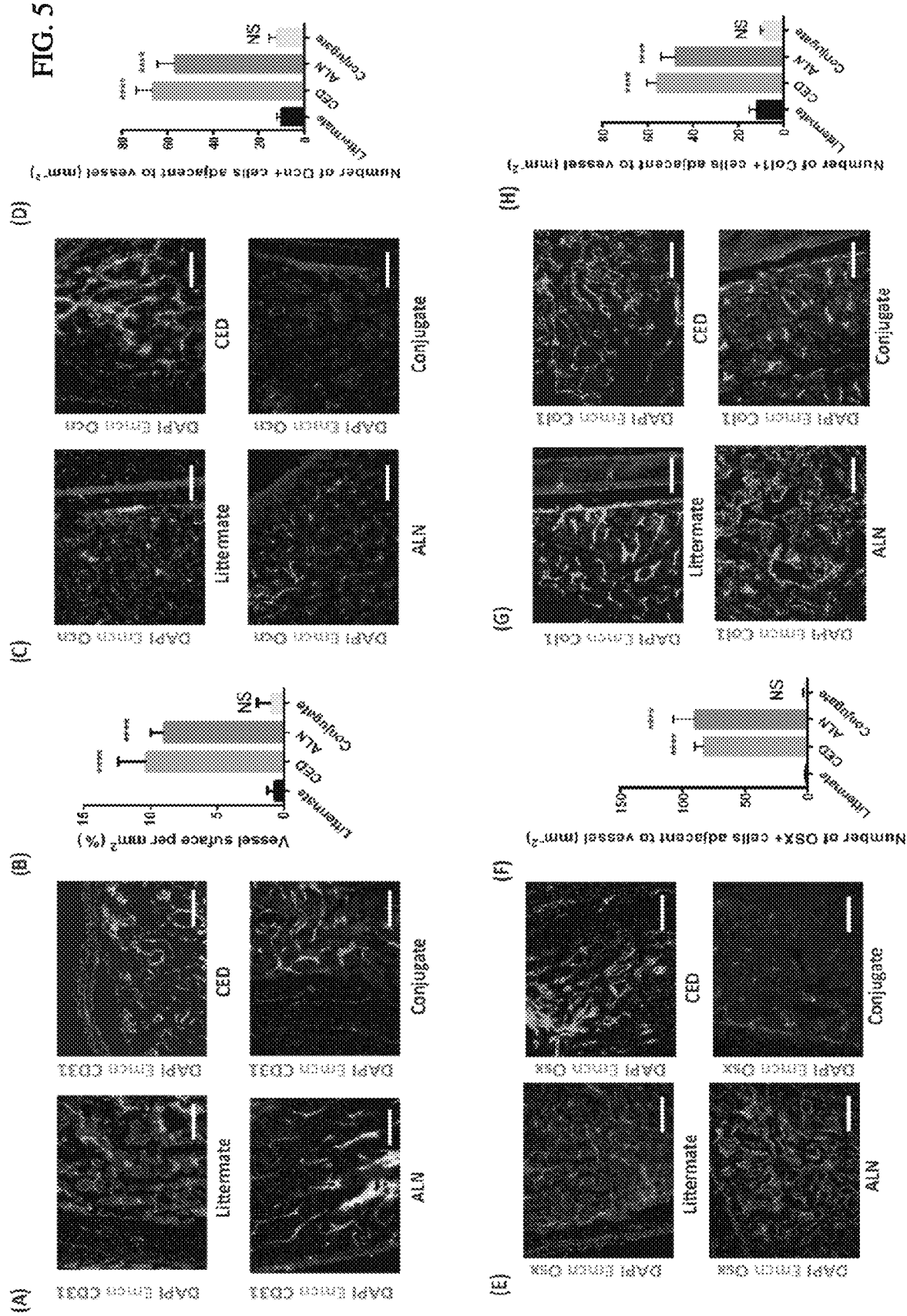

FIG. 5 presents graphs showing that TGF-β-induced formation of type H vessels leads to osteoblastic differentiation. Part (A) shows immunofluorescence staining of CD31$^+$ (red) and Emcn$^+$ (green) cells in tibia sections. Part (B) shows quantification data of vessel surface in (A). Part (C) shows immunofluorescence staining of Ocn$^+$ (red) and Emcn$^+$ (green) cells in tibia sections. Part (D) presents quantification data of Ocn$^+$ cells adjacent to vessels in (C). Part (E) shows immunofluorescence staining of Osx$^+$ (red) and Emcn$^+$ (green) cells in tibia sections. Part (F) presents quantification data of Osx$^+$ cells adjacent to vessels in (E). Part (G) shows immunofluorescent staining of Col11 (red) and Emcn$^+$ (green) cells in tibia sections. Part (H) presents quantification of Col1$^+$ cells adjacent to vessels in (G). In FIG. 5, the following conventions are used: NS, not significant. P<0.01, *P<0.001, ****P<0.0001 determined by multifactorial ANOVA. All data are reported as the mean±s.d.

Figure 6:
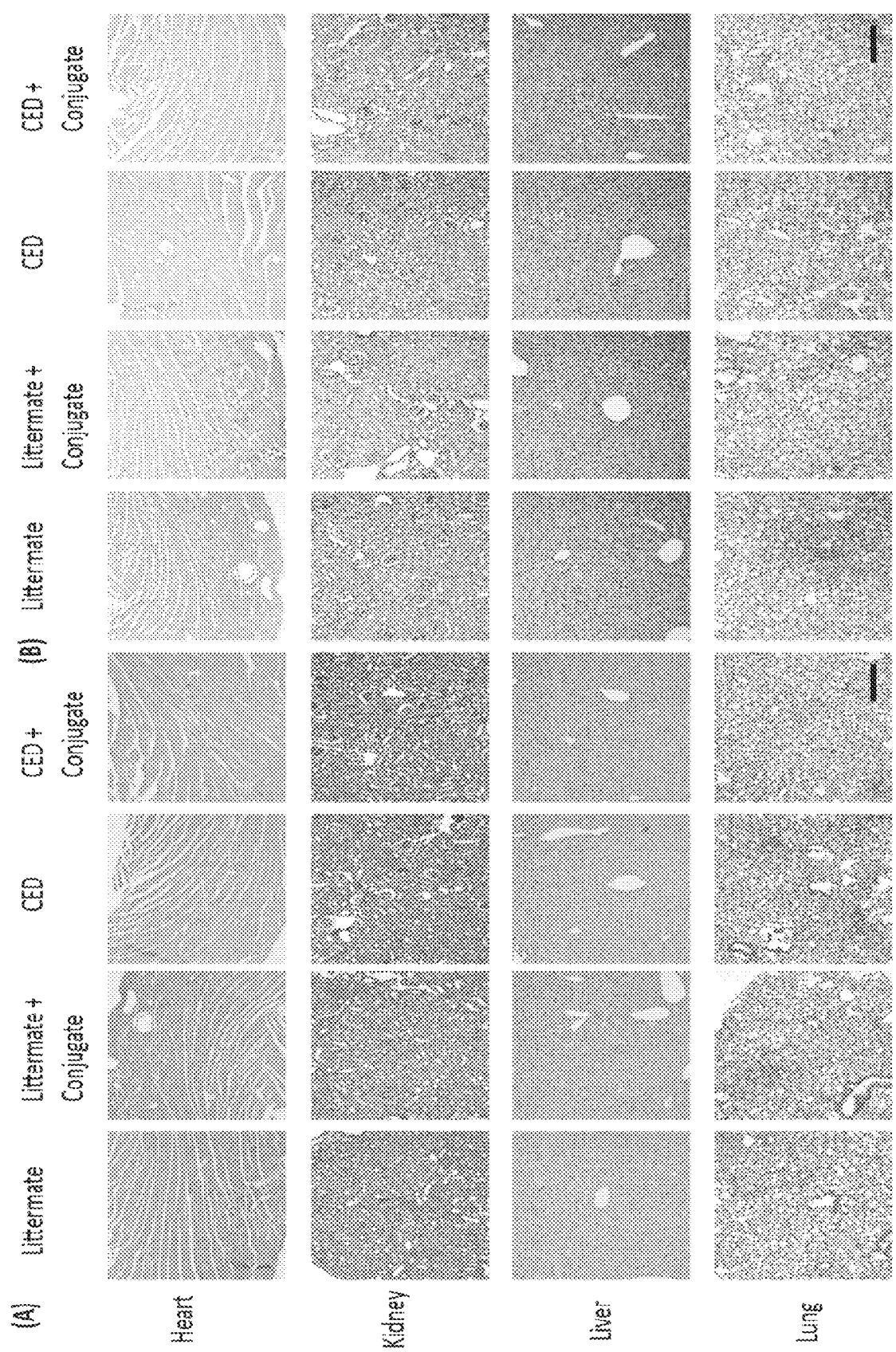

FIG. 6 presents pictures showing that administration of a conjugate of the present disclosure, Compound 1, does not affect other organs. Part (A) shows HE staining of heart, liver, kidney, and lung. Part (B) shows pSmad2/3 staining of heart, liver, kidney, and lung.

DETAILED DESCRIPTION OF THE INVENTION

In various embodiments, the present disclosure is generally related to novel bisphosphonate conjugates. The conjugates of the present disclosure typically attach a TGF-beta inhibitor to a bisphosphonate either directly or via a metabolically cleavable linker. Without wishing to be bound by theories, it is believed that the bisphosphonate unit can selectively deliver the conjugates to the bones, due to its intrinsic bone-affinity. Thus, the conjugates herein can be particularly useful for treating bone related diseases or disorders where inhibition of TGF-beta mediated signaling is beneficial, e.g., as described herein. Any TGF-beta inhibitor with a suitable group that can be linked to the bisphosphonate, either directly or through a linker, can be used, with a preference for inhibitors with a low $IC_{50}$ value (e.g., comparable (or better) activities with known TGF-beta inhibitors such as LY2109761 or SD-208). The inhibitor and bisphosphonate can be linked directly, e.g., via an amide bond, or through a linker that can be metabolically cleaved in the bones such as subchondral bones (or vicinity thereof). As used herein, the term "bone(s)" should be broadly construed as encompassing bone tissues, cells, matrices, surfaces, cavities, and the like. Preferably, the conjugates herein releases TGF-beta inhibitors "locally" such as to the bones such as subchondral bones or the vicinity to inhibit TGF-beta mediated signaling. The structures of the conjugates herein can also be adjusted, e.g., by modifying the linker, to release the TGF-beta inhibitor to a site (e.g., the bones such as subchondral bones) at a desired rate.

As used herein, unless specified or otherwise obvious from context, the phrase "TGF-beta inhibitor" should be understood as encompassing any compound that inhibits TGF beta mediated signaling in a cell relative to vehicle, or otherwise counter the effect mediated by TGF beta mediated signaling. For example, as used herein, TGF-beta inhibitors should be understood as encompassing any known TGF-beta receptor (Type I, II, or III) inhibitors such as LY2109761. In some embodiments, TGF-beta inhibitors can include any compound that reduces pSmad 2/3 level or Smad 2/3 expression in a cell relative to vehicle. In some embodiments, TGF-beta inhibitors can also encompass an inhibitor that does not directly inhibit the interaction between TGF-beta and its receptors, but nonetheless reduces or inhibits TGF beta mediated signaling in a cell relative to vehicle. In some embodiments, TGF-beta inhibitors can also encompass an inhibitor of a downstream event mediated by TGF beta mediated signaling, such as an integrin inhibitor. In any of the embodiments described herein, unless otherwise specified or contradictory, TGF beta (or TGFβ) can be TGF beta-1 (or TGFβ1).

The conjugates of the present disclosure are useful for treating various diseases or disorders as described herein, for example, bone diseases or disorders, such as Camurati-Engelmann disease (CED) or osteoarthritis.

CED is a chromosomal dominant genetic disorder. It is caused by the mutations in the chromosomal region 19q13 that encodes the latency-associated peptide (LAP) of transforming growth factor-β1 (TGF-β1). The mutations in the LAP cause TGF-β1 activation upon secretion in bone marrow, which disrupts bone resorption from formation. About 98% of patients show typical long bone dysplasia, while 54% and 63% show deformities in the skull and pelvis, respectively. Glucocorticoids and alendronate are the most common therapies for CED patients; however, these drugs only relieve bone pain and fatigue and do not effectively attenuate CED progression. It was demonstrated that aberrantly activated TGF-β1 drove CED progression. By systematic TGF-β type 1 receptor inhibitor (TβR1I) administration, bone morphology and uncoupled bone remodeling was shown to be rescued in CED mouse model. Because TGF-β1 receptors are widely expressed and broadly affect other functions, systemic administration of TβR1I can cause serious side effects, such as immune response and angiogenesis. Thus, delivering TβRII to bone with the conjugates of the present disclosure (e.g., Compound 1) can reduce its side effects and increase efficacy in CED treatment.

Aberrant activation of TGF-β by osteoclasts on subchondral bone is at onset of osteoarthritis and may also be an important source of pain in OA and progression. Specifically, subchondral bone marrow edema-like lesions visualized by magnetic resonance imaging (MRI) are highly correlated with OA progression and pain. Zoledronic acid, a bisphosphonate drug that inhibits osteoclast activity, was effective in reducing OA knee pain and bone marrow edema-like lesion size. Analysis of a comprehensive dataset from the National Institutes of Health Osteoarthritis Initiative showed that bisphosphonate users experienced significantly reduced knee pain at years 2 and 3. Increased subchondral bone remodeling occurs during OA progression. It was reported previously that aberrant subchondral bone remodeling initiates joint articular cartilage degeneration. Specifically, elevated osteoclast activity activates excessive TGF-β1 to recruit mesenchymal stem cells in the marrow, where they undergo aberrant subchondral bone formation. Systemic or local administration of TGF-β-neutralizing antibody (1D11) attenuated OA progression by targeting subchondral bone pathological features. The subchondral bone changes at the onset of OA further suggest a potential pathogenesis of OA pain. Thus, delivering TβRII to bone with the conjugates of the present disclosure (e.g., Compound 1) can attenuate OA progression and pain.

Conjugates

In some embodiments, the present disclosure provides a compound of Formula I, or a pharmaceutically acceptable ester thereof, or a pharmaceutically acceptable salt thereof,

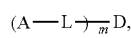

$$(A-L)_m-D,$$ Formula I wherein

A at each occurrence is independently a residue of a bisphosphonate, e.g., having a structure of

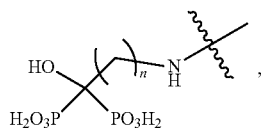

wherein n is an integer of 1-10;

L at each occurrence is independently null or a metabolically cleavable linker;

m is 1, 2, or 3; and

D is a residue of a TGFβ inhibitor that is capable of attaching to L-A, for example, in some embodiments, D is characterized as having a Formula II:

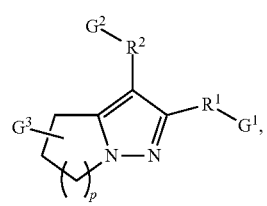

wherein $G^1$, $G^2$, and $G^3$ are each independently hydrogen or a connecting group, e.g., a group capable of forming an ester or amide bond with an L-A unit, wherein at least one of $G^1$, $G^2$, and $G^3$ is directly attached to an L-A unit of Formula I, wherein p is 1, 2, or 3; and $R^1$ and $R^2$ are each independently an optionally substituted phenylene or an optionally substituted heteroarylene.

In some embodiments, the conjugates herein can exist as an ester of the compound of Formula I, typically a pharmaceutically acceptable ester. For example, in some embodiments, the bisphosphonate moiety can be masked with one or more ester bonds (such as $C_{1-4}$ alkyl esters). When administered, the ester bonds can be metabolically cleaved in vivo to release the compound of Formula I, or a salt thereof, or a metabolite thereof.

In some embodiments, the conjugates herein can exist as a salt of the compound of Formula I, e.g., a pharmaceutically acceptable salt. In particular, in some embodiments, the bisphosphonate group can exist in the form of a base addition salt, such as a sodium salt.

In some embodiments, the compound of Formula I can exist as an internal salt, e.g., having a zwitterion ion structure. For example, when D contains a basic nitrogen atom, the compound of Formula I may form an internal salt with a zwitterion structure. Such internal salts are also within the scope of the present invention.

Typically, m in Formula I is 1, and the compound has a structure of Formula I-1,

$$A-L-D,$$ Formula I-1 wherein A, L, and D are defined herein.

In some embodiments, A in Formula I (e.g., Formula I-1) can be a residue of an amino-bisphosphonate compound, which includes any known bisphosphonate which has a secondary or primary amine functionality. Non-limiting useful bisphosphonates include alendronic acid, 4-amino-1-hydroxybutylidene-1,1-bisphosphonic acid; alendronate (also known as alendronate sodium or alendronate monosodium trihydrate), 4-amino-1-hydroxybutylidene-1,1-bisphosphonic acid monosodium trihydrate; alendronic acid and alendronate are described in U.S. Pat. No. 4,922,007, to Kieczykowski et al., issued May 1, 1990; U.S. Pat. No. 5,019,651, to Kieczykowski et al., issued May 28, 1991; U.S. Pat. No. 5,510,517, to Dauer et al., issued Apr. 23, 1996; U.S. Pat. No. 5,648,491, to Dauer et al., issued Jul. 15, 1997; 6-amino-1-hydroxyhexylidene-1,1-bisphosphonic acid (neridronate); 3-amino-1-hydroxypropylidene-1,1-bisphosphonic acid (pamidronate); or pharmaceutically acceptable salts thereof, or mixtures thereof. As used herein, the "residue" of a bisphosphonate refers to the portion of the bisphosphonate that is linked to an L-D unit of Formula I (e.g., Formula I-1), e.g., via an amino group.

In some embodiments, A in Formula I (e.g., Formula I-1) can be

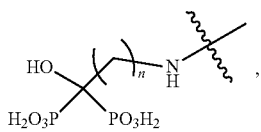

wherein n can be an integer of 1-10 (e.g., 1-6), preferably, n is 1, 2, or 3, more preferably, n is 3.

In some embodiments, the linker L in Formula I (e.g., Formula I-1) can be null. Thus, in some embodiments, the bisphosphonate residue A can be directly attached to the inhibitor residue D, for example, via an amide bond,

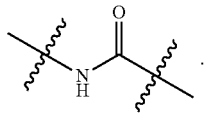 [SMILES: *NC(*)=O]

In some embodiments, the linker L in Formula I (e.g., Formula I-1) is a metabolically cleavable linker, which connects the bisphosphonate residue A with the inhibitor residue D. The term "metabolically cleavable linker" should be understood as including any group that can be metabolically cleaved, for example, which allows the linkage of L-A and/or L-D in the compound of Formula I (e.g., Formula I-1) to be metabolically cleaved (e.g., in vitro or in vivo), for example, to release the TGF-beta inhibitor from which D is derived, and/or the bisphosphonate, or metabolites thereof. In some embodiments, the metabolically cleavable liner is such that, when tested in an in vitro or in vivo method such as those described in the Examples section, the compound of Formula I can be metabolically cleaved to release a TGF-beta inhibitor, e.g., an inhibitor that can inhibit phosphorylation of Smad2/3 or the expression level of Smad2/3, e.g., in the bone such as subchondral bone. In some embodiments, L is a linker such that the compound of Formula I (e.g., Formula I-1), or pharmaceutically acceptable ester thereof, or a pharmaceutically acceptable salt thereof, is capable of in vivo releasing, e.g., after administration to a human subject, a TGF-beta inhibitor having a formula of D-Y, a salt thereof, or a metabolite thereof, wherein D is as defined herein, and Y is hydrogen when the attaching atom of D is oxygen or nitrogen, or hydroxyl when the attaching atom of D is carbon from C(=O).

Various metabolically cleavable linkers are suitable for Formula I. For example, the metabolically cleavable linker L, together with the directly attached atom/group from D or A, can form an ester, amide, carbamate, or urea, which can be metabolically cleaved. For example, in some embodiments, the linker L in Formula I (e.g., Formula I-1) can be a carbonyl group, which attaches to an oxygen or nitrogen atom of D and a nitrogen atom of A:

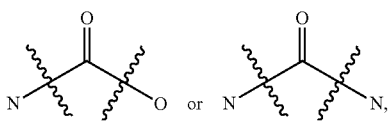

in other words, A and D are connected to form a carbamate or urea. The carbamate or urea can be metabolically cleaved to release D-H and/or A-H, wherein D and A are defined herein, and H refers to hydrogen.

In some embodiments, the linker L can connect with D and A through the same or a different type of metabolically cleavable bonds. For example, in some embodiments, L-A can be joined through an amide, carbamate, or urea, and L-D can be joined through an ester, amide, carbamate, or urea.

In some embodiments, L is a linker of Formula III,

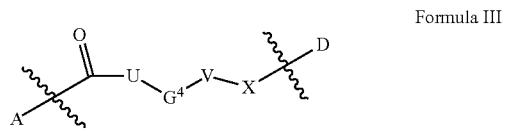

Formula III wherein

U and V are each independently —O—, —O-$G^5$-, —NH—, —NH-$G^6$-, —N($C_{1-6}$ alkyl)-, —N($C_{1-6}$ alkyl)-$G^7$-, an optionally substituted alkylene (e.g., a $C_{1-6}$ alkylene (such as a $C_{2-4}$ alkylene), which is optionally substituted), an optionally substituted heteroalkylene (e.g., a $C_{1-6}$ heteroalkylene (such as a $C_{2-4}$ heteroalkylene), which can include 1 or 2 independently selected heteroatoms (e.g., oxygen or nitrogen atoms), and which is optionally substituted), optionally substituted cycloalkylene (e.g., a $C_{3-6}$ cycloalkylene, which is optionally substituted), optionally substituted heterocyclylene (e.g., a 5-8 membered heterocyclylene, which is optionally substituted), optionally substituted arylene (e.g., a phenylene, which is optionally substituted), optionally substituted heteroarylene (e.g., a 5-10 membered heteroarylene, which is optionally substituted), or null;

$G^4$, $G^5$, $G^6$, and $G^7$ are each independently an optionally substituted alkylene (e.g., a $C_{1-6}$ alkylene (such as a $C_{2-4}$ alkylene), which is optionally substituted), an optionally substituted heteroalkylene (e.g., a $C_{1-6}$ heteroalkylene (such as a $C_{2-4}$ heteroalkylene), which can include 1 or 2 independently selected heteroatoms (e.g., oxygen or nitrogen atoms), and which is optionally substituted), optionally substituted cycloalkylene (e.g., a $C_{3-6}$ cycloalkylene, which is optionally substituted), optionally substituted heterocyclylene (e.g., a 5-8 membered heterocyclylene, which is optionally substituted), optionally substituted arylene (e.g., a phenylene, which is optionally substituted), optionally substituted heteroarylene (e.g., a 5-10 membered heteroarylene, which is optionally substituted) or null; and X is C(=O) or null. Typically, when the attaching atom from D is an oxygen or nitrogen atom, X is C(=O). However, for the present disclosure, other definitions are allowed so long as the TGF-beta inhibitor, or a metabolite thereof, from which D is derived, can be metabolically released, such as in vivo released.

As used herein, an "optionally substituted alkylene" should be understood broadly to encompass a divalent radical where one or more alkylene carbons form a cycloalkyl, heterocyclyl, aryl, or heteroaryl ring, either in the internal position(s) or at the terminal position(s) of the chain, which ring can be further optionally substituted. For example, "optionally substituted alkylene" should be understood as encompassing

or

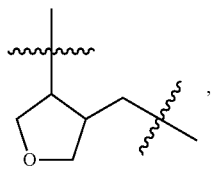 [SMILES: *CC1COCC1*]

and the like. Similarly, as used herein, an "optionally substituted heteroalkylene" should be understood broadly to encompass a divalent radical where one or more heteroalkylene carbon and/or heteroatoms form a cycloalkyl, heterocyclyl, aryl, or heteroaryl ring, either in the internal position(s) or at the terminal position(s) of the chain, which ring can be further optionally substituted. For example, "optionally substituted heteroalkylene" should be understood as encompassing

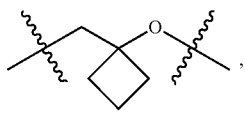 [SMILES: *CC1(O*)CCC1]

or

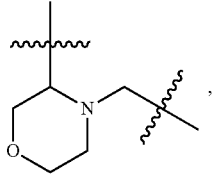 [SMILES: *CN1CCOCC1*]

and the like.

In some specific embodiments, L is

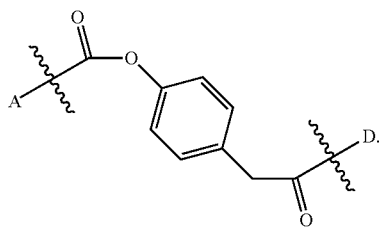

In some embodiments, D attaches to L through an oxygen or nitrogen atom.

In some embodiments, D is a residue of a TGF-beta inhibitor, which has one or more groups that can attach to the L-A unit in Formula I (e.g., Formula I-1). For example, any of the TGF-beta inhibitors that are known, which include an OH, NH, NH$_2$, or COOH group are suitable. Some exemplary TGF-beta inhibitors are described, for example, in U.S. Pat. Nos. 7,087,626, 7,368,445, 7,511,056, 7,265,225, 9,617,243, and U.S. Publication No. 2006/0079680, the content of each of which is incorporated herein by reference in its entirety. As used herein, the "residue" of a TGF-beta inhibitor refers to the portion of the TGF-beta inhibitor that is linked to an L-A unit in Formula I (e.g., Formula I-1). Examples of such residues are described herein.

In some embodiments, D is a residue of a pyrrazole based TGF-beta inhibitor. For example, in some embodiments, D is characterized as having a Formula II:

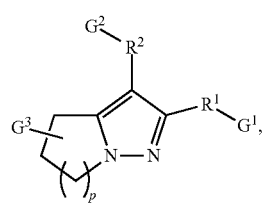

Formula II wherein $G^1$, $G^2$, and $G^3$ are each independently hydrogen or a connecting group, e.g., a group capable of forming an ester or amide bond with an L-A unit, wherein at least one of $G^1$, $G^2$, and $G^3$ is directly attached to an L-A unit in Formula I, wherein p is 1, 2, or 3; and $R^1$ and $R^2$ are each independently an optionally substituted phenylene or an optionally substituted heteroarylene.

In some embodiments, p is 1.

The connecting group for $G^1$, $G^2$, and $G^3$ can be monovalent or divalent, depending on whether the group is directly attached to a unit of L-A. For example, in some embodiments, each of $G^1$, $G^2$, and $G^3$ can be an independently selected divalent radical, with one end directly attached to $R^1$, $R^2$, or the bicyclic pyrrazole ring in Formula II, respectively, and the other end directly attached to a unit of L-A. It should be noted that if more than one L-A units are present in Formula I, each L-A unit can be independently selected. In some embodiments, two of $G^1$, $G^2$, and $G^3$ can be an independently selected divalent radical, with one end directly attached to $R^1$, $R^2$, or the bicyclic pyrrazole ring in Formula II, respectively, and the other end directly attached to a unit of L-A. In some embodiments, only one of $G^1$, $G^2$, and $G^3$ can be a divalent radical, with one end directly attached to $R^1$, $R^2$, or the bicyclic pyrrazole ring in Formula II, respectively, and the other end directly attached to a unit of L-A. In some embodiments, the non-attaching $G^1$, $G^2$, and $G^3$ is/are hydrogen. In some embodiments, the non-attaching $G^1$, $G^2$, and $G^3$ is/are a monovalent connecting group, which is capable of forming a bond with a unit of L-A, such as an OH, NH, NH$_2$, COOH, or CONH$_2$ group.

Various divalent radicals are suitable for use as connecting groups. For example, in some embodiments, the $G^1$, $G^2$, and/or $G^3$ attaching to L-A can be independently a divalent radical of Formula IV:

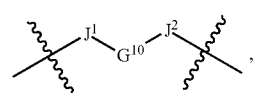

Formula IV wherein $J^1$ and $J^2$ are each independently —O—, —NH—, —N(C$_{1-6}$ alkyl)-, —C(=O)—, —OC(=O)—, —N(H)C(=O)—, —N(C$_{1-6}$ alkyl)C(=O)—, or null, and $G^{10}$ is an optionally substituted alkylene (e.g., a C$_{1-6}$ alkylene (such as a C$_{2-4}$ alkylene), which is optionally substituted), an optionally substituted heteroalkylene (e.g., a C$_{1-6}$ heteroalkylene (such as a C$_{2-4}$ heteroalkylene), which can include 1 or 2 independently selected heteroatoms (e.g., oxygen or nitrogen atoms), and which is optionally substituted), optionally substituted cycloalkylene (e.g., a $C_{3-6}$ cycloalkylene, which is optionally substituted), optionally substituted heterocyclylene (e.g., a 5-8 membered heterocyclylene, which is optionally substituted), optionally substituted arylene (e.g., a phenylene, which is optionally substituted), optionally substituted heteroarylene (e.g., a 5-10 membered heteroarylene, which is optionally substituted), or null. For example, in some embodiments, the divalent radical can be —O—($C_{2-4}$ alkylene)-O—, —O—($C_{2-4}$ alkylene)-N(H)—, —O—($C_{2-4}$ alkylene)-N($C_{1-6}$ alkyl)-, —O—($C_{1-4}$ alkylene)-C(=O)—, —N(H)—($C_{1-4}$ alkylene)-C(=O)—, or —N($C_{1-6}$ alkyl)-($C_{1-4}$ alkylene)-C(=O)—, wherein the alkylene is optionally substituted.

In some embodiments, the $G^1$, $G^2$, and/or $G^3$ attaching to L-A can be —O—, —NH—, —N($C_{1-6}$ alkyl)-, or —C(=O)—.

In some embodiments, D can be a radical of Formula IIa, IIb, or IIc:

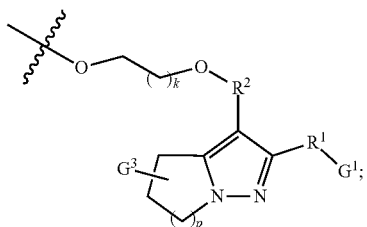

Formula IIa

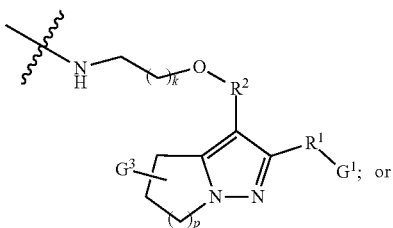

Formula IIb

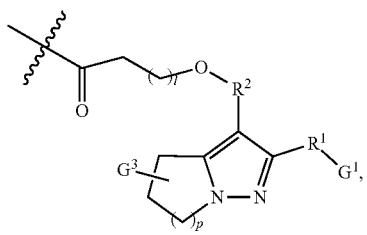

Formula IIc wherein each k is independently an integer of 1-6, and l is an integer of 0-6. In some embodiments, p is 1. In some embodiments, $G^1$ and $G^3$ are hydrogen. In some embodiments, D is a radical of Formula IIa, wherein k is 1 or 2. In some embodiments, D is a radical of Formula IIb, wherein k is 1 or 2. In some embodiments, D is a radical of Formula IIc, wherein l is 0, 1, or 2.

In some embodiments, $R^1$ can be an optionally substituted heteroarylene. For example, in some embodiments, $R^1$ can be an optionally substituted 5 or 6 membered heteroarylene, for example, a pyridinylene, such as 2,4-, 2,5-, or 2,6-pyridinylene:

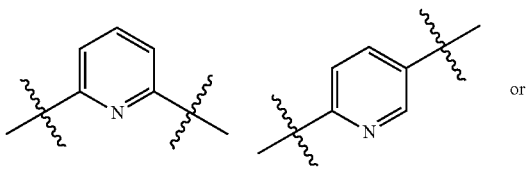

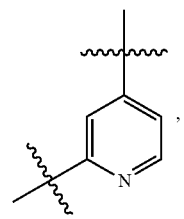

which is optionally substituted at the remaining positions, for example, with 1, 2, or 3 substituents each independently halogen, hydroxyl, an optionally substituted $C_{1-4}$ alkyl, or an optionally substituted $C_{1-4}$ alkoxy.

In some embodiments, $R^2$ can be an optionally substituted heteroarylene. For example, in some embodiments, $R^2$ can be an optionally substituted 8-10 membered heteroarylene. In some embodiments, $R^2$ can be an optionally substituted quinolinylene, such as 4,6-, 4,7-, or 4,8-quinolinylene:

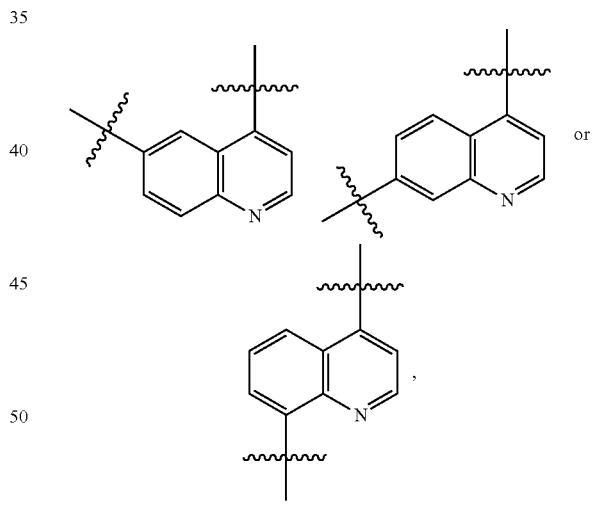

which is optionally substituted at the remaining positions, for example, with 1, 2, 3, or 4 substituents each independently halogen, hydroxyl, an optionally substituted $C_{1-4}$ alkyl, or an optionally substituted $C_{1-4}$ alkoxy. Other heteroarylenes are also suitable, which include for example, pyrrolopyrimidinylene, pyrrolopyridinylene, pyrazolopyridinylene, etc. Examples of TGF beta inhibitors containing such heterocyclic structure motifs can be found for example in U.S. Pat. No. 7,511,056.

In some embodiments, $R^1$ is pyridinylene, $G^1$ and $G^3$ are hydrogen, and p is 1, and D is characterized by a Formula IId:

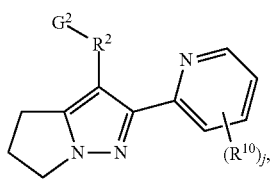

Formula IId wherein $R^2$, $R^{10}$, $G^2$ and j are defined herein. In some embodiments, $R^{10}$ at each occurrence is independently halogen, hydroxyl, an optionally substituted $C_{1-4}$ alkyl, or an optionally substituted $C_{1-4}$ alkoxy; and j is an integer of 0-3. In some embodiments, $R^2$ is an optionally substituted 8-10 membered heteroarylene (e.g., described herein). In some embodiments, $G^2$ is

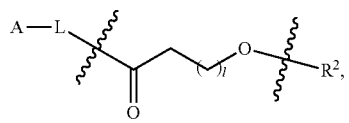

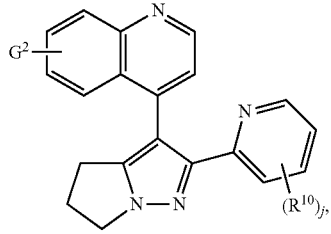

wherein each k is independently an integer of 1-6 (e.g., 1 or 2), and 1 is an integer of 0-6 (e.g., 0, 1, or 2).

In some embodiments, $R^2$ is quinolinylene, $G^1$ and $G^3$ are hydrogen, and p is 1, and D is characterized by a Formula IIe:

Formula IIe

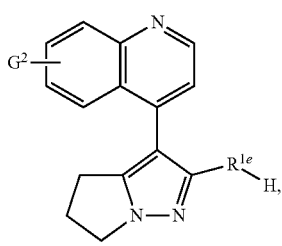

wherein $G^2$ is defined herein, and $R^{1e}$ is an optionally substituted phenylene or an optionally substituted 5 or 6-membered heteroarylene. In some embodiments, $G^2$ is

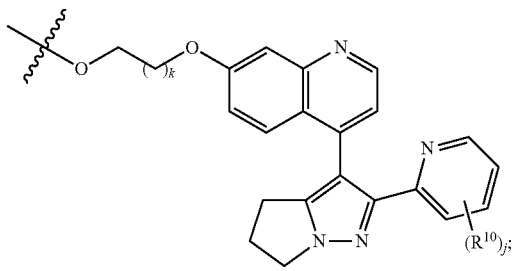

wherein each k is independently an integer of 1-6 (e.g., 1 or 2), and 1 is an integer of 0-6 (e.g., 0, 1, or 2).

In some embodiments, $G^1$ and $G^3$ are hydrogen, and p is 1, and D is characterized as having a Formula IIf:

Formula IIf

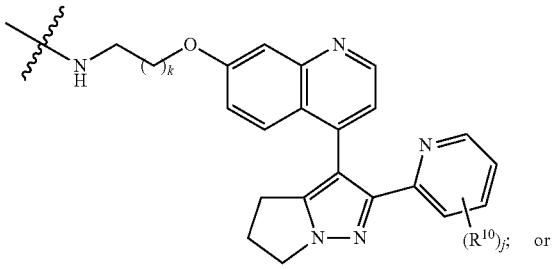

wherein $R^{10}$, $G^2$ and j are defined herein. In some embodiments, $R^{10}$ at each occurrence is independently halogen, hydroxyl, an optionally substituted $C_4$ alkyl, or an optionally substituted $C_{1-4}$ alkoxy; and j is an integer of 0-3. In some embodiments, j is 0. In some embodiments, j is 1, and $R^{10}$ can be a $C_{1-4}$ alkyl.

In some embodiments, D is characterized as having a Formula IIg, IIh, or IIi:

Formula IIg

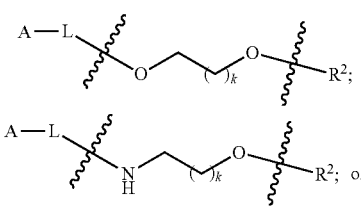

Formula IIh

-continued

Formula IIi

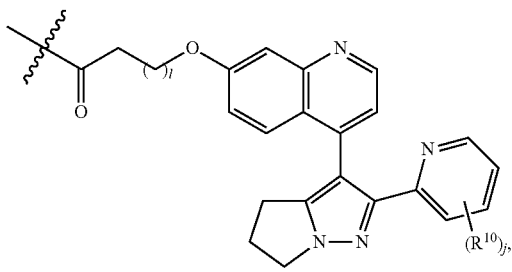

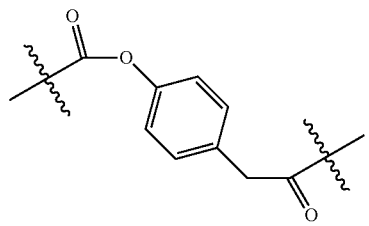

wherein $R^{10}$, j, k, and l are defined herein. In some embodiments, $R^{10}$ at each occurrence is independently halogen, hydroxyl, an optionally substituted $C_{1-4}$ alkyl, or an optionally substituted $C_{1-4}$ alkoxy; and j is an integer of 0-3. In some embodiments, each k is 1 or 2, and l is 0, 1, or 2. In some embodiments, j is 0. In some embodiments, j is 1, and $R^{10}$ can be a $C_{1-4}$ alkyl.

It should be noted that any of the definitions of D, A, or L described herein can be combined with any of the definitions of the others of D, A, and L as described herein. Such combinations are specifically contemplated and are within the scope of this invention.

For example, in some embodiments, the compound of Formula I is characterized by Formula I-2, I-3, or I-4:

Formula I-2

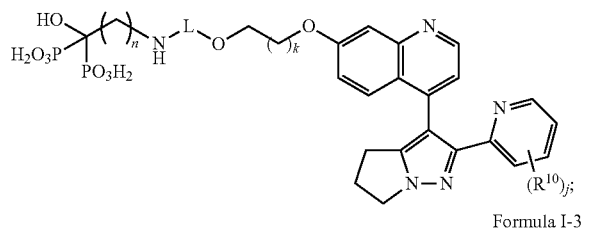

Formula I-3

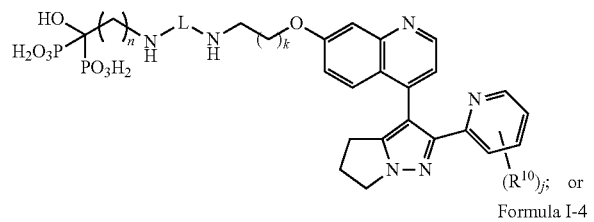

Formula I-4

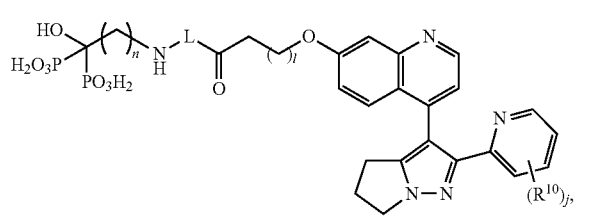

wherein L, n, k, l, $R^{10}$, and j are defined herein. In some embodiments, L is C(=O). In some embodiments, L in Formula I-4 can be null. In some embodiments, L can be a radical of Formula III. In some embodiments, L can be In some embodiments, n is 1, 2, or 3. In some embodiments, k in Formula I-2 or I-3 is 1 or 2. In some embodiments, l in Formula I-4 is 0, 1, or 2. In some embodiments, j is 0. In some embodiments, j is 1 and $R^{10}$ can be a $C_{1-4}$ alkyl.

In some specific embodiments, the present disclosure also provides a compound selected from:

(Compound 1)

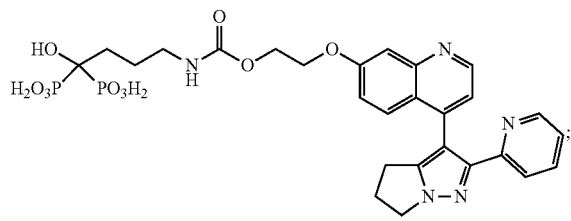

(Compound 2)

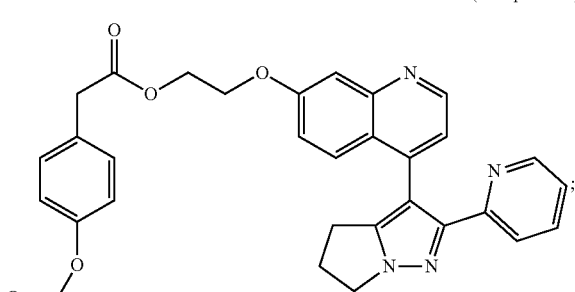

(Compound 3)

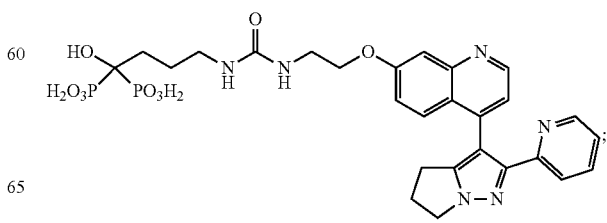

(Compound 5)

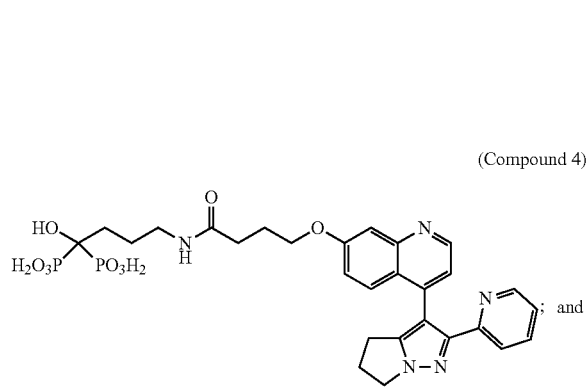

(Compound 4)

a pharmaceutically acceptable ester thereof, a zwitterion thereof, or a pharmaceutically acceptable salt thereof.

Method of Synthesis

The conjugates of the present disclosure can be readily synthesized by those skilled in the art in view of the present disclosure. Two exemplified synthesis are also shown in the Examples section.

The following synthetic processes as shown in Schemes 1 and 2 for certain compounds of Formula I-2 are illustrative, which can be applied similarly by those skilled in the art for the synthesis of other compounds of Formula I.

Scheme 1

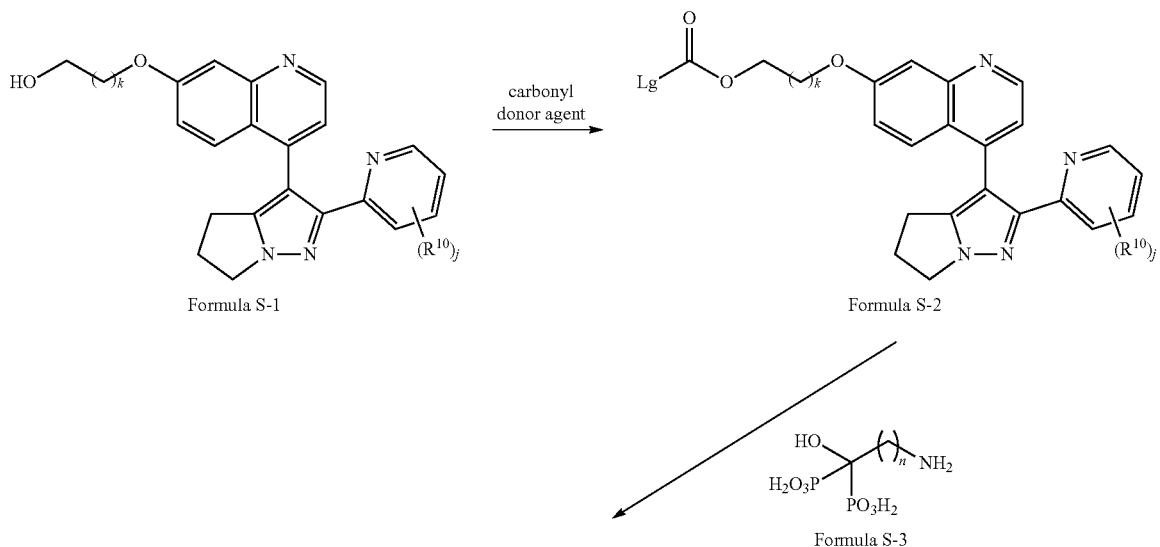

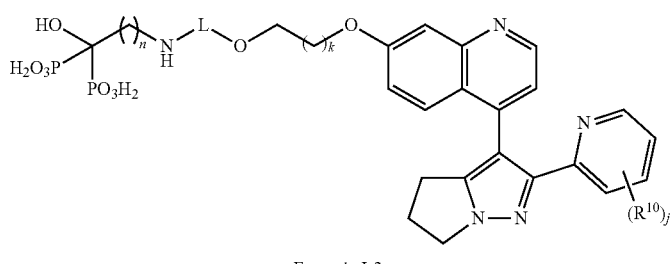

Formula I-2

Thus, a TGF-beta inhibitor compound of Formula S-1 can first react with a carbonyl donor agent (such as 4-nitrophenyl chloroformate) to form a compound of Formula S-2, wherein Lg is a leaving group (such as 4-nitrophenol). The compound of Formula S-2 can then react with a bisphosphonate of Formula S-3 to form a compound of Formula I-2 (wherein L is C(=O)). $R^{10}$, j, n, and k in Scheme 1 are as defied herein. Compounds of Formula S-1 can be readily prepared, for example, by following procedures similar to those described in the literature, such as in U.S. Pat. Nos. 7,265,225 and 7,087,626 or the exemplary procedure described herein.

In some embodiments, L in Formula I-2 is a linker of Formula III. Such compounds can be prepared, for example, by first converting a compound of Formula S-1 with appropriate reagents into a compound of Formula S-4, which can involve more than 1 step. See Scheme 2. For example, see also Example 2, the hydroxyl group of Formula S-1 can first form an ester linkage (X is C(=O)) to form a compound of Formula S-4 (e.g., in Example 2, X is C(=O), V is $CH_2$, $G^4$ is phenylene, and U is O), wherein Pg is a protecting group or hydrogen. The compound of Formula S-4, optionally after a deprotecting step to convert a non-hydrogen Pg into hydrogen, can then be converted into a compound of Formula S-5 with a carbonyl donor agent, wherein Lg in Formula S-5 represents a leaving group, such as 4-nitrophenol. Similar to those described in Scheme 1, the compound of Formula S-5 can then react with a bisphosphonate of Formula S-3 to form the compound of Formula I-2 wherein L is a linker of Formula III. The variables such as Pg, U, $G^4$, V, X, $R^{10}$, j, n, and k in Scheme 2 are as defied herein.

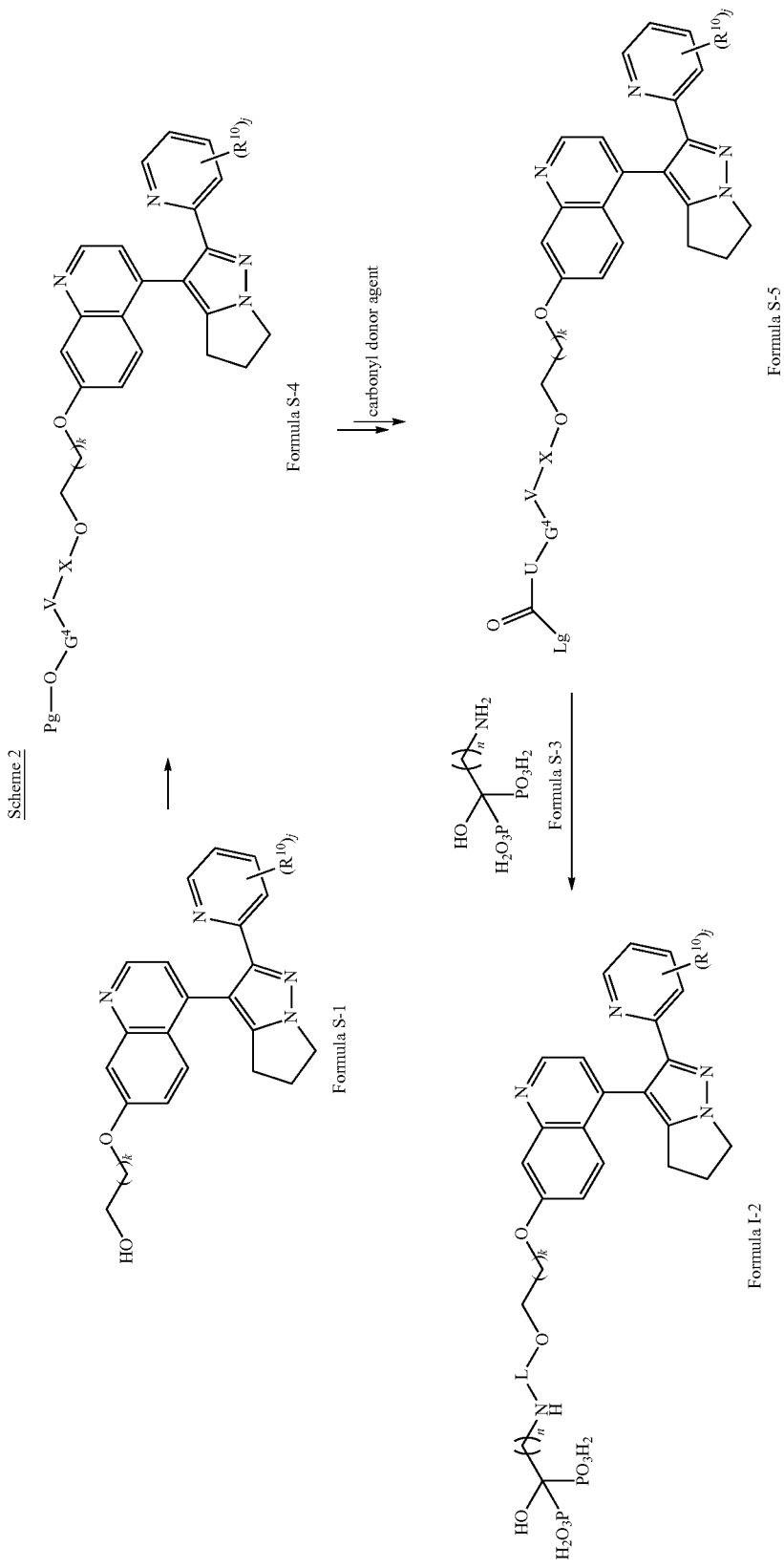

Other compounds of Formula I can be prepared similarly. For example, compounds of Formula I-3, wherein L is C(=O) or Formula III, can be prepared analogously to procedures described in Schemes 1 and 2, e.g., in the case of L is C(=O), by reacting an appropriate starting material with a carbonyl donor agent, which can then be coupled with a bisphosphonate of Formula S-3 to form the compound of Formula I-3. Similarly, compounds of Formula I-4 can be prepared by coupling the TGF-beta inhibitor with an appropriate agent through an ester or amide bond formation with the carbonyl group of the inhibitor, and coupling the bisphosphonate with an appropriate agent through an amide, carbamate, or urea bond formation with the nitrogen of the bisphosphonate. Ester, amide, carbamate, and urea bond formation conditions include any of those known in the art.

As will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in "Protective Groups in Organic Synthesis", $4^{th}$ ed. P. G. M. Wuts; T. W. Greene, John Wiley, 2007, and references cited therein. The reagents for the reactions described herein are generally known compounds or can be prepared by known procedures or obvious modifications thereof. For example, many of the reagents are available from commercial suppliers such as Aldrich Chemical Co. (Milwaukee, Wisconsin, USA), Sigma (St. Louis, Missouri, USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplemental (Elsevier Science Publishers, 1989), Organic Reactions, Volumes 1-40 (John Wiley and Sons, 1991), March's Advanced Organic Chemistry, (Wiley, $7^{th}$ Edition), and Larock's Comprehensive Organic Transformations (Wiley-VCH, 1999).

Pharmaceutical Compositions

Certain embodiments are directed to a pharmaceutical composition comprising one or more of the conjugates of the present disclosure.

The pharmaceutical composition can optionally contain a pharmaceutically acceptable excipient. In some embodiments, the pharmaceutical composition comprises a conjugate of the present disclosure (e.g., a compound of Formula I (e.g., Formula I-1, Formula I-2, Formula I-3, Formula I-4, or any of Compounds 1-5) or a pharmaceutically acceptable ester thereof, or a pharmaceutically acceptable salt thereof) and a pharmaceutically acceptable excipient. Pharmaceutically acceptable excipients are known in the art. Non-limiting suitable excipients include, for example, encapsulating materials or additives such as absorption accelerators, antioxidants, binders, buffers, carriers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof. See also Remington's The Science and Practice of Pharmacy, 21st Edition, A. R. Gennaro (Lippincott, Williams & Wilkins, Baltimore, Md., 2005; incorporated herein by reference), which discloses various excipients used in formulating pharmaceutical compositions and known techniques for the preparation thereof.

The pharmaceutical composition can include any one or more of the conjugates of the present disclosure. For example, in some embodiments, the pharmaceutical composition comprises a compound of any of Formula I, Formula I-1, I-2, I-3, or I-4, or any of Compounds 1-5, a pharmaceutically acceptable ester thereof, or a pharmaceutically acceptable salt thereof, e.g., in a therapeutically effective amount. In any of the embodiments described herein, the pharmaceutical composition can comprise a therapeutically effective amount of Compound 1, a pharmaceutically acceptable ester thereof, or a pharmaceutically acceptable salt thereof.

The pharmaceutical composition can also be formulated for delivery via any of the known routes of delivery, which include but are not limited to oral, parenteral, inhalation, etc.

In some embodiments, the pharmaceutical composition can be formulated for oral administration. The oral formulations can be presented in discrete units, such as capsules, pills, cachets, lozenges, or tablets, each containing a predetermined amount of the active compound; as a powder or granules; as a solution or a suspension in an aqueous or non-aqueous liquid; or as an oil-in-water or water-in-oil emulsion. Excipients for the preparation of compositions for oral administration are known in the art. Non-limiting suitable excipients include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, and mixtures thereof.

In some embodiments, the pharmaceutical composition is formulated for parenteral administration (such as intravenous injection or infusion). The parenteral formulations can be, for example, an aqueous solution, a suspension, or an emulsion. Excipients for the preparation of parenteral formulations are known in the art. Non-limiting suitable excipients include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof.

In some embodiments, the pharmaceutical composition is formulated for inhalation. The inhalable formulations can be, for example, formulated as a nasal spray, dry powder, or an aerosol administrable through a metered-dose inhaler. Excipients for preparing formulations for inhalation are known in the art. Non-limiting suitable excipients include, for example, lactose, talc, silicic acid, aluminum hydroxide, calcium silicates and polyamide powder, and mixtures of these substances. Sprays can additionally contain propellants, such as chlorofluorohydrocarbons and volatile unsubstituted hydrocarbons, such as butane and propane.

The pharmaceutical composition can include various amounts of the conjugates of the present disclosure, depending on various factors such as the intended use and potency of the conjugates and/or the underlying TGF beta inhibitor.

In some embodiments, the pharmaceutical composition comprises a therapeutically effective amount of a conjugate of the present disclosure. In some embodiments, the pharmaceutical composition comprises a therapeutically effective amount of the conjugate of the present disclosure and a pharmaceutically acceptable excipient. As used herein, a therapeutically effective amount of a conjugate of the present disclosure is an amount effective to treat a disease or disorder as described herein, which can depend on the recipient of the treatment, the disease or disorder being treated and the severity thereof, the composition containing the compound, the time of administration, the route of administration, the duration of treatment, the compound potency (or the potency of the underlying TGF beta inhibitor), its rate of clearance and whether or not another drug is co-administered.

Method of Treatment

TGF-beta mediated signaling has been shown to be associated with various diseases or disorders. TGF-β family signaling is of special relevance in mesenchymal differentiation, including bone development. Deregulated expression or activation of components of this signaling system can contribute to skeletal diseases, e.g. osteoarthritis. It was also shown that aberrant TGF-beta activities, e.g., enhanced level of TGF-beta such as in subchondral bones, can lead to various bone remodeling related bone diseases or disorders. Xu et al. *Bone Research* 6:2 (2018). For example, excessive activation of TGF-beta can lead to aberrant bone formation, for example, in the subchondral bone and can affect multiple joint tissues. Genetic disorders such as Camurati-Engelmann disease (CED), Marfan syndrome, Loeys-Dietz syndrome, Shprintzen-Goldberg syndrome, and neurofibromatosis type 1 were also shown to involve aberrant TGF-beta signaling. Aberrant TGF-beta activities have been shown to be associated with various organ fibrosis, cancer metastasis (such as bone metastasis), etc.

Various inhibitors of TGF-beta signaling have been shown to be effective in treating different diseases, including in clinical trials. For example, LY2109761 was shown to reduce a potential of bone metastasis in mice; and SD-208 was shown to be effective in treating mice with bone metastases. Further, Tang Y. et al. has shown that intraperitoneal injection of a TGF beta receptor inhibitor (SB505124) rescued bone remodeling defects in CED mice, with the treated group showing less tibial fractures and with significantly reduced cortical thickness, porosity, osteoblasts surface and osteoclasts surfaces. *Nat Med.* 15:757-765 (2009). Thus, evidence also supports the use of TGF beta inhibitor for the treatment of bone diseases or disorders that are associated with aberrations in bone remodeling, which include, but are not limited to, osteoarthritis, Camurati-Engelmann disease (CED), hyperparathyroidism, Paget's disease, multiple myeloma, osteoporosis, and osteopetrosis. See also, Zhen, G. et al., *Nat Med.* 19(6):704-712 (2013), which describes that inhibition of TGF-beta signaling in subchondral bone is useful for treating osteoarthritis; Xie, L. et al., *Ann N Y Acad Sci.* 1376(1):53-64 (2016), which discloses systemic neutralization of excessive TGF-beta ligands with TGF-beta-neutralizing antibody (1D11) effectively prevented osteoarthritis progression in animal models; see also Tang Y. et al., *Nat Med.* 15:757-765 (2009).

Current non-surgical treatments for CED mainly focus on relieving pain; however, there is no effective treatment to attenuate disease progression in bone. The most common prescriptions for CED are glucocorticoids, steroids that stimulate apoptosis of osteoblasts and osteocytes and inhibit osteoblastic differentiation. Glucocorticoids also increase the expression and activation of TGF-β1. Furthermore, long-term treatment with steroids impairs linear growth in children and decreases bone mineral density. Anti-TGF-β receptor monoclonal antibodies also serve as a potential treatment; however, TGF-β receptor is widely distributed in the body, and antibodies systemic administration cause side effects, such as immune suppression and inflammation. The conjugates of the present disclosure (e.g., Compound 1) provide an alternative for bone-specific CED treatment.

As shown in the Examples section, HE and pSmad2/3 staining show that the conjugates of the present disclosure, represented by Compound 1, delivered a TβR1I specifically to bone, where it released over time. The conjugate effectively attenuated CED progression at a dose of 100 μg/kg per week compared with 10 mg/kg per day of TβR1I by intraperitoneal injection in a previous literature report. The total dose of TβR1I was reduced by 700 times after bone-targeting modification. The effective dose ranged from 100 μg/kg to 1 mg/kg per week, supporting the use of several doses in future clinical applications. According to pharmaceutical data, 50-70% of alendronate reaches bone in less than 2 hours, and the rest is excreted in urine. As also shown in the Examples section, with Western blotting and immunofluorescence staining, the conjugates of the present disclosure, represented by Compound 1, start to release TβR1I after 24 hours in cells. The sustained release of TβR1I decreases the inhibition of non-bone TGF-β signaling. Overall, the bone-targeted delivery and sustained release of TβR1I can improve the safety and efficacy of the drug, and reduce laborious manipulations in the clinic.

During adulthood, bone undergoes constant remodeling, a process that follows a well-established cycle that occurs at specific anatomical sites along the bone surface. In CED, TGF-β1 activation disrupts normal bone remodeling in an incorrect temporal-spatial manner. As shown in the Examples section, while a single injection of TβR1I, Compound S-3, (100 g/kg) did not inhibit TGF-β1 signaling; the same dose of conjugate (Compound 1) significantly reduced the number of pSmad2/3$^+$ cells in a time-dependent manner.

In summary, it was shown that the conjugates of the present disclosure can deliver TβR1I specifically to bone. By inhibiting TGF-β signaling, the conjugates of the present disclosure, represented by Compound 1, restored normal bone remodeling in CED mice with no obvious side effects. The results, together with evidence from previously published reports, support that the bone-targeting conjugates of the present disclosure (e.g., Compound 1) can provide an advantageous alternative treatment for CED and other aberrant bone remodeling diseases, such as Osteoarthritis, Paget's disease and osteopetrosis.

Accordingly, in some embodiments, the present disclosure also provides a method of treating diseases or disorders associated with aberrant TGF-beta activity. Suitable diseases or disorders associated with aberrant TGF-beta activity to be treated with the methods herein include any of those known in the art, for example, fibrosis, cancer metastasis, osteoarthritis, CED, etc. In some embodiments, the disease or disorder is a bone disease or disorder, such as bone metastasis, osteoarthritis, CED, hyperparathyroidism, Paget's disease, multiple myeloma, osteoporosis, or osteopetrosis. In some embodiments, the method comprises administering a therapeutically effective amount of a conjugate of the present disclosure (e.g., a compound of any of Formula I, Formula I-1, I-2, I-3, or I-4, or any of Compounds 1-5, a pharmaceutically acceptable ester thereof, or a pharmaceutically acceptable salt thereof), or a pharmaceutical composition comprising the conjugate of the present disclosure to a subject in need of such treatment. The conjugate of the present disclosure or the pharmaceutical composition can be administered to the subject via various routes. For example, in some embodiments, the administering is an oral administration. In some embodiments, the administering can be an injection, such as intravenous, intramuscular, intracutaneous, subcutaneous, intraduodenal, or intraperitoneal injection. In some embodiments, the administering can be an infusion, such as an intravenous infusion. In some embodiments, the administering comprises inhalation. The conjugate of the present disclosure or the pharmaceutical composition can be administered to the subject via a suitable dosing regimen, for example, for as long as the treatment is needed. The therapeutically effective amount of the conjugate of the present disclosure can be an amount effective to treat the respective disease or disorder as described herein (e.g., osteoarthritis), which can depend on the recipient of the treatment, the disease or disorder being treated and the severity thereof, the composition containing the compound, the time of administration, the route of administration, the duration of treatment, the compound potency (or the potency of the underlying TGF beta inhibitor), its rate of clearance and whether or not another drug is co-administered. In some embodiments, the conjugate can be any of Compounds 1-5, or a pharmaceutically acceptable ester thereof, or a pharmaceutically acceptable salt thereof. In any of the embodiments described herein, the conjugate can be Compound 1, or a pharmaceutically acceptable ester thereof, or a pharmaceutically acceptable salt thereof.

In some embodiments, the present disclosure also provides a method of treating a bone disease or disorder associated with bone remodeling. For example, in some embodiments, the bone disease or disorder is osteoarthritis, CED, hyperparathyroidism, Paget's disease, multiple myeloma, osteoporosis, or osteopetrosis. In some specific embodiments, a method of treating osteoarthritis is provided. In some embodiments, the method comprises administering a therapeutically effective amount of a conjugate of the present disclosure (e.g., a compound of any of Formula I, Formula I-1, I-2, I-3, or I-4, or any of Compounds 1-5, a pharmaceutically acceptable ester thereof, or a pharmaceutically acceptable salt thereof), or a pharmaceutical composition comprising the conjugate of the present disclosure to a subject in need of such treatment. The conjugate of the present disclosure or the pharmaceutical composition can be administered to the subject via various routes. For example, in some embodiments, the administering is an oral administration. In some embodiments, the administering can be an injection, such as intravenous, intramuscular, intracutaneous, subcutaneous, intraduodenal, or intraperitoneal injection. In some embodiments, the administering can be an infusion, such as an intravenous infusion. In some embodiments, the administering comprises inhalation. The conjugate of the present disclosure or the pharmaceutical composition can be administered to the subject via a suitable dosing regimen, for example, for as long as the treatment is needed. In some embodiments, the conjugate can be any of Compounds 1-5, or a pharmaceutically acceptable ester thereof, or a pharmaceutically acceptable salt thereof. In some embodiments, the conjugate can be Compound 1, or a pharmaceutically acceptable ester thereof, or a pharmaceutically acceptable salt thereof.

The conjugates of the present disclosure can also be used to deliver TGF-beta inhibitor to a subject in need thereof. For example, the present disclosure has experimentally shown that the conjugates herein, represented by Compound 1, can be selectively delivered to the bone and release the respective TGF-beta inhibitor in an amount effective to inhibit TGF-beta mediated signaling. Accordingly, in some embodiments, the present disclosure also provides a method of delivering a TGF-beta inhibitor to a subject in need thereof. In some embodiments, the method comprises administering to the subject a compound of Formula I (e.g., a compound of Formula I-1, I-2, I-3, or I-4, or any of Compounds 1-5) as defined herein, or a pharmaceutically acceptable ester thereof, or a pharmaceutically acceptable salt thereof, or a pharmaceutical composition comprising the compound, or pharmaceutically acceptable ester thereof, or pharmaceutically acceptable salt thereof, as defined herein. In some embodiments, the administering comprises administration via injection or infusion, oral administration, or inhalation. In some embodiments, the administering delivers and/or releases an effective amount of the TGF-beta inhibitor to the bones such as subchondral bones and/or the vicinity of the subject. In some embodiments, the subject suffers from osteoarthritis. In some embodiments, the subject suffers from bone metastasis, osteoarthritis, CED, hyperparathyroidism, Paget's disease, multiple myeloma, osteoporosis, or osteopetrosis, or other diseases or disorders described herein.

Definitions

It is meant to be understood that proper valences are maintained for all moieties and combinations thereof.

It is also meant to be understood that a specific embodiment of a variable moiety herein may be the same or different as another specific embodiment having the same identifier.

Suitable groups for A, L, and D in compounds of Formula I (e.g., Formula I-1 to I-4) are independently selected. The described embodiments of the present invention may be combined. Such combination is contemplated and within the scope of the present invention. For example, it is contemplated that embodiments for any of A, L, and D can be combined with embodiments defined for any other of A, L, and D.

The symbol, ᧪ whether utilized as a bond or displayed perpendicular to (or otherwise crossing) a bond, indicates the point at which the displayed moiety is attached to the remainder of the molecule. It should be noted that in some chemical drawings herein, the immediately connected group or groups are shown outside the symbol, ᧪ to indicate connectivity, as would be understood by those skilled in the art. For example, in a definition of $G^2$, $R^2$ and L-A can be included in the drawings to indicate connectivity, such as

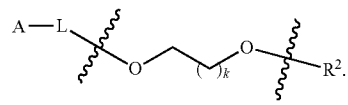

However, unless obvious from context, when no such groups are shown in a definition, such as a definition of the attaching $G^1$, $G^2$ or $G^3$ group as Formula IV

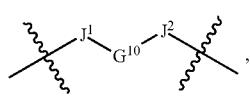

then it should be understood that either direction of connection (left to right, or right to left) is allowed, so long as it is consistent with the other definitions herein.

As used herein, the term "conjugate(s) of the present disclosure" refers to any of the compounds described herein according to Formula I (e.g., Formula I-1, Formula I-2, Formula I-3, Formula I-4, or any of Compounds 1-5), isotopically labeled compound(s) thereof (such as a deuterated analog wherein one of the hydrogen atoms is substituted with a deuterium atom with an abundance above its natural abundance), possible stereoisomers thereof (including diastereoisomers, enantiomers, and racemic mixtures), tautomers thereof, conformational isomers thereof, possible zwitterions thereof, esters thereof (such as pharmaceutically acceptable esters), and/or pharmaceutically acceptable salts thereof (e.g., acid addition salt such as HCl salt or base addition salt such as Na salt). Hydrates and solvates of the conjugates of the present disclosure are considered compositions of the present disclosure, wherein the compound(s) is in association with water or solvent, respectively.

As used herein, the phrase "administration" of a compound, "administering" a compound, or other variants thereof means providing the compound or a prodrug (e.g., an ester prodrug) of the compound to the individual in need of treatment.

As used herein, the term "alkyl" as used by itself or as part of another group refers to a straight- or branched-chain aliphatic hydrocarbon. In some embodiments, the alkyl which can include one to twelve carbon atoms (i.e., $C_{1-12}$ alkyl) or the number of carbon atoms designated (i.e., a $C_1$ alkyl such as methyl, a $C_2$ alkyl such as ethyl, a $C_3$ alkyl such as propyl or isopropyl, etc.). In one embodiment, the alkyl group is a straight chain $C_{1-10}$ alkyl group. In another embodiment, the alkyl group is a branched chain $C_{3-10}$ alkyl group. In another embodiment, the alkyl group is a straight chain $C_{1-6}$ alkyl group. In another embodiment, the alkyl group is a branched chain $C_{3-6}$ alkyl group. In another embodiment, the alkyl group is a straight chain $C_{1-4}$ alkyl group. Non-limiting exemplary $C_{1-4}$ alkyl groups include methyl, ethyl, propyl, isopropyl, butyl, sec-butyl, tert-butyl, and iso-butyl. As used herein, the term "alkylene" as used by itself or as part of another group refers to a divalent radical derived from an alkyl group. For example, non-limiting straight chain alkylene groups include —$CH_2$—$CH_2$—, $CH_2$—$CH_2$—, —$CH_2$—$CH_2$—$CH_2$—, —$CH_2$—$CH_2$—, and the like.

As used herein, the term "optionally substituted alkyl" or "optionally substituted alkylene" as used by itself or as part of another group means that the alkyl or alkylene as defined above is either unsubstituted or substituted with one or more (e.g., one, two, or three) substituents each independently chosen from, e.g., halo (e.g., F), oxo, nitro, cyano, $OR^a$, $CO_2R^a$, $OCO_2R^a$, $OSO_2NR^bR^c$, $SO_3R^a$, $OSO_3R^a$, $OS(O)_nR^e$, $NR^bR^c$, $C(=O)NR^bR^c$, $OC(=O)NR^bR^c$, $SO_2NR^bR^c$, $OC(=O)R^d$, $C(=O)R^d$, $S(O)_nR^e$, $C(=NR)NR^bR^c$, alkyl, heteroalkyl, cycloalkyl, alkenyl, alkynyl, aryl, heteroaryl, and heterocyclyl, wherein each alkyl, heteroalkyl, cycloalkyl, alkenyl, alkynyl, aryl, heteroaryl, and heterocyclyl is further optionally substituted with 1-5 $R^g$, wherein n is 0, 1, or 2, and $R^a$, $R^b$, $R^c$, $R^d$, $R^e$, $R^f$ and $R^g$ are defined herein. In one embodiment, the optionally substituted alkyl is substituted with three substituents, e.g., three fluorines. In one embodiment, the optionally substituted alkyl is substituted with one substituent. In one embodiment, the optionally substituted alkyl is substituted with two substituents.

As used herein, each of $R^a$, $R^d$ and $R^e$ at each occurrence is independently selected from hydrogen, $C_{1-10}$ alkyl, $C_{1-10}$ heteroalkyl with 1-3 independently selected heteroatoms (such as O, N, S), $C_{1-10}$ haloalkyl, $C_{2-10}$ alkenyl, $C_{2-10}$ alkynyl, $C_{3-10}$ cycloalkyl, 3-14 membered heterocyclyl, $C_{6-14}$ aryl, and 5-14 membered heteroaryl, wherein each alkyl, heteroalkyl, alkenyl, alkynyl, carbocyclyl, heterocyclyl, aryl, and heteroaryl is independently substituted with 0, 1, 2, 3, 4, or 5 $R^g$ groups.

As used herein, each of $R^b$, $R^c$ and $R^f$ at each occurrence is independently selected from hydrogen, nitro, cyano, $OR^{aa}$, $CO_2R^{aa}$, $SO_3R^{aa}$, $NR^{bb}R^{cc}$, $C(=O)NR^bR^c$, $SO_2NR^{bb}R^{cc}$, $OC(=O)R^{dd}$, $C(=O)R^{dd}$, $S(O)_nR^{ee}$, $C(=NR^{ff})NR^{bb}R^{cc}$, $C_{1-10}$ alkyl, $C_{1-10}$ heteroalkyl with 1-3 independently selected heteroatoms (such as O, N, S), $C_{1-10}$ haloalkyl, $C_{2-10}$ alkenyl, $C_{2-10}$ alkynyl, $C_{3-10}$ cycloalkyl, 3-14 membered heterocyclyl, $C_{6-14}$ aryl, and 5-14 membered heteroaryl, or $R^b$ and $R^c$, or $R^f$ and one of $R^b$ and $R^c$, are joined to form a 3-14 membered heterocyclyl or 5-14 membered heteroaryl ring, wherein each alkyl, heteroalkyl, alkenyl, alkynyl, carbocyclyl, heterocyclyl, aryl, and heteroaryl is independently substituted with 0, 1, 2, 3, 4, or 5 $R^g$ groups, wherein n is 0, 1, or 2, and $R^{aa}$, $R^{bb}$, $R^{cc}$, $R^{dd}$, $R^{ee}$ and $R^{ff}$ are defined herein. In some embodiments, at least one of $R^b$ and $R^c$ is chosen from hydrogen, $C_{1-10}$ alkyl, $C_{1-10}$ haloalkyl, $C_{2-10}$ alkenyl, $C_{2-10}$ alkynyl, $C_{3-10}$ cycloalkyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^g$ groups. In some embodiments, both $R^b$ and $R^c$ are independently chosen from hydrogen, $C_{1-10}$ alkyl, $C_{1-10}$ haloalkyl, $C_{2-10}$ alkenyl, $C_{2-10}$ alkynyl, $C_{3-10}$ cycloalkyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^g$ groups.

As used herein, $R^g$ at each occurrence is independently selected from halo (e.g., F), nitro, cyano, $OR^{aa}$, $CO_2R^{aa}$, $NR^{bb}R^{cc}$, $C(=O)NR^{bb}R^{cc}$, $SO_2NR^{bb}R^{cc}$, $NR(SO_2NR^{bb}R^{cc})$, $OSO_2NR^{bb}R^{cc}$, $NR^{bb}(SO_3R^{aa})$, $SO_3R^{aa}$, $OSO_3R^{aa}$, $NR^{bb}(S(O)_nR^{ee})$, $O(S(O)_nR^{ee})$, $OC(=O)R^{dd}$, $OCO_2R^{aa}$, $NR^{bb}CO_2R^{aa}$, $OC(=O)NR^{bb}R^{cc}$, $NR^{bb}(C(=O)R^{dd})$, $C(=O)R^{dd}$, $S(O)_nR^{ee}$, $C(=NR^{ff})NR^{bb}R^{cc}$, —$NR^{hh}$—$C(=O)NR^{bb}R^{cc}$, —$NR^{hh}$—$C(=NR^{ee})NR^{bb}R^{cc}$, $C_{1-6}$ alkyl, $C_{1-6}$ heteroalkyl with 1-2 independently selected heteroatoms (such as O, N, S), $C_{1-6}$ haloalkyl, $C_{2-6}$ alkenyl, $C_{2-6}$ alkynyl, $C_{3-10}$ cycloalkyl, $C_{6-10}$ aryl, 3-10 membered heterocyclyl, 5-10 membered heteroaryl, wherein each alkyl, heteroalkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{gg}$ substituents can be joined to form =O or =S, wherein n is 0, 1, or 2, and $R^{aa}$, $R^{bb}$, $R^{cc}$, $R^{dd}$, $R^{ee}$, $R^{ff}$, $R^{gg}$ and $R^{hh}$ are defined herein.

As used herein, each of $R^{aa}$, $R^{bb}$, $R^{cc}$, $R^{dd}$, $R^{ee}$, $R^{ff}$ and $R^{hh}$ at each occurrence is independently selected from hydrogen, $C_{1-4}$ alkyl, $C_{1-6}$ heteroalkyl with 1-2 independently selected heteroatoms (such as O, N, S), $C_{1-6}$ haloalkyl, $C_{2-6}$ alkenyl, $C_{2-6}$ alkynyl, $C_{3-6}$ cycloalkyl, 4-6 membered heterocyclyl, $C_{6-10}$ aryl, and 5-10 membered heteroaryl, or $R^{bb}$ and $R^{cc}$, $R^{ff}$ and $R^{hh}$, $R^{ff}$ and one of $R^{bb}$ and $R^{cc}$, or $R^{hh}$ and one of $R^{bb}$ and $R^{cc}$, are joined to form a 4-6 membered heterocyclyl or 5-10 membered heteroaryl ring, wherein each alkyl, heteroalkyl, alkenyl, alkynyl, carbocyclyl, heterocyclyl, aryl, and heteroaryl is independently substituted with 0, 1, 2, 3, 4, or 5 $R^{gg}$ groups.

As used herein, $R^{gg}$ at each occurrence is independently selected from halo (e.g., F), nitro, cyano, hydroxy, $NH_2$, $N(H)(C_{1-6}$ alkyl), $N(C_{1-6}$ alkyl)($C_{1-6}$ alkyl), $N(H)(C_{3-6}$ cycloalkyl), $N(C_{1-6}$ alkyl)($C_{3-6}$ cycloalkyl), $N(C_{3-6}$ cycloalkyl)($C_{3-6}$ cycloalkyl), O—$C_{1-6}$ alkyl, $C_{1-6}$ alkyl, $C_{1-6}$ heteroalkyl with 1-2 independently selected heteroatoms (such as O, N, S), $C_{1-6}$ haloalkyl, O—$C_{1-6}$ haloalkyl, $C_{3-6}$ cycloalkyl optionally substituted with 1-5 substituents independently selected from halogen, $C_{1-4}$ alkyl, and $C_{3-6}$ cycloalkyl, O—$C_{3-6}$ cycloalkyl optionally substituted with 1-5 substituents independently selected from halogen, $C_{1-4}$ alkyl, and $C_{3-6}$ cycloalkyl, 4-6 membered heterocyclyl optionally substituted with 1-3 substituents independently selected from halogen, oxo, $C_{1-4}$ alkyl, and $C_{3-6}$ cycloalkyl, $C_{6-10}$ aryl optionally substituted with 1-5 substituents independently selected from halogen, cyano, $C_{1-4}$ alkyl, and $C_{3-6}$ cycloalkyl, and 5-10 membered heteroaryl optionally substituted with 1-5 substituents independently selected from halogen, cyano, $C_{1-4}$ alkyl, and $C_{3-6}$ cycloalkyl, or two geminal $R^{gg}$ substituents can be joined to form =O or =S.

As used herein, the term "cycloalkyl" as used by itself or as part of another group refers to saturated and partially unsaturated (containing one or two double bonds) cyclic aliphatic hydrocarbons containing one to three rings having from three to twelve carbon atoms (i.e., $C_{3-12}$ cycloalkyl) or the number of carbons designated. In one embodiment, the cycloalkyl group has two rings. In one embodiment, the cycloalkyl group has one ring. In another embodiment, the cycloalkyl group is a $C_{3-8}$ cycloalkyl group. In another embodiment, the cycloalkyl group is a $C_{3-6}$ cycloalkyl group. Non-limiting exemplary cycloalkyl groups include cyclopropyl, cyclobutyl, cyclopentyl, cyclohexyl, cycloheptyl, cyclooctyl, norbornyl, decalin, adamantyl, cyclopentenyl, and cyclohexenyl. As used herein, the term "cycloalkylene" as used by itself or as part of another group refers to a divalent radical derived from a cycloalkyl group, for example,

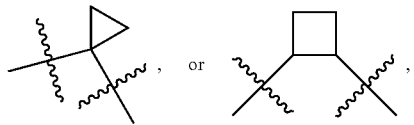 [SMILES: *C1(*)CC1 ; *C1CCC1*]

etc.

As used herein, the term "optionally substituted cycloalkyl" or "optionally substituted cycloalkylene" as used by itself or as part of another group means that the cycloalkyl or cycloalkylene as defined above is either unsubstituted or substituted with one or more (e.g., one, two, or three) substituents each independently chosen from, e.g., halo (e.g., F), oxo, nitro, cyano, $OR^a$, $CO_2R^a$, $OCO_2R^a$, $OSO_2NR^bR^c$, $SO_3R^a$, $OSO_3R^a$, $OS(O)_nR^e$, $NR^bR^c$, C(=O)$NR^bR^c$, OC(=O)$NR^bR^c$, $SO_2NR^bR^c$, OC(=O)$R^d$, C(=O)$R^d$, $S(O)_nR^e$, C(=$NR^f$)$NR^bR^c$, alkyl, heteroalkyl, cycloalkyl, alkenyl, alkynyl, aryl, heteroaryl, and heterocyclyl, wherein each alkyl, heteroalkyl, cycloalkyl, alkenyl, alkynyl, aryl, heteroaryl, and heterocyclyl is further optionally substituted with 1-5 $R^g$, wherein n is 0, 1, or 2, and $R^a$, $R^b$, $R^c$, $R^d$, $R^e$, $R^f$ and $R^g$ are defined herein. In one embodiment, the optionally substituted cycloalkyl is substituted with three substituents. In one embodiment, the optionally substituted cycloalkyl is substituted with two substituents. In another embodiment, the optionally substituted cycloalkyl is substituted with one substituent.

As used herein, the term "alkenyl" as used by itself or as part of another group refers to an alkyl group as defined above containing one, two or three carbon-to-carbon double bonds. In one embodiment, the alkenyl group is a $C_{2-6}$ alkenyl group. In another embodiment, the alkenyl group is a $C_{2-4}$ alkenyl group. Non-limiting exemplary alkenyl groups include ethenyl, propenyl, isopropenyl, butenyl, sec-butenyl, pentenyl, and hexenyl.

As used herein, the term "optionally substituted alkenyl" as used herein by itself or as part of another group means the alkenyl as defined above is either unsubstituted or substituted with one or more (e.g., one, two, or three) substituents each independently chosen from, e.g., halo (e.g., F), oxo, nitro, cyano, $OR^a$, $CO_2R^a$, $OCO_2R^a$, $OSO_2NR^bR^c$, $SO_3R^a$, $OSO_3R^a$, $OS(O)_nR^e$, $NR^bR^c$, C(=O)$NR^bR^c$, OC(=O)$NR^bR^c$, $SO_2NR^bR^c$, OC(=O)$R^d$, C(=O)$R^d$, $S(O)_nR^e$, C(=$NR^f$)$NR^bR^c$, alkyl, heteroalkyl, cycloalkyl, alkenyl, alkynyl, aryl, heteroaryl, and heterocyclyl, wherein each alkyl, heteroalkyl, cycloalkyl, alkenyl, alkynyl, aryl, heteroaryl, and heterocyclyl is further optionally substituted with 1-5 $R^g$, wherein n is 0, 1, or 2, and $R^a$, $R^b$, $R^c$, $R^d$, $R^e$, $R^f$ and $R^g$ are defined herein.

As used herein, the term "alkynyl" as used by itself or as part of another group refers to an alkyl group as defined above containing one to three carbon-to-carbon triple bonds. In one embodiment, the alkynyl has one carbon-carbon triple bond. In one embodiment, the alkynyl group is a $C_{2-6}$ alkynyl group. In another embodiment, the alkynyl group is a $C_{2-4}$ alkynyl group. Non-limiting exemplary alkynyl groups include ethynyl, propynyl, butynyl, 2-butynyl, pentynyl, and hexynyl groups.

As used herein, the term "optionally substituted alkynyl" as used herein by itself or as part of another group means the alkynyl as defined above is either unsubstituted or substituted with one or more (e.g., one, two, or three) substituents each independently chosen from, e.g., halo (e.g., F), oxo, nitro, cyano, $OR^a$, $CO_2R^a$, $OCO_2R^a$, $OSO_2NR^bR^c$, $SO_3R^a$, $OSO_3R^a$, $OS(O)_nR^c$, $NR^bR^c$, C(=O)$NR^bR^c$, OC(=O)$NR^bR^c$, $SO_2NR^bR^c$, OC(=O)$R^d$, C(=O)$R^d$, $S(O)_nR^e$, C(=$NR^f$)$NR^bR^c$, alkyl, heteroalkyl, cycloalkyl, alkenyl, alkynyl, aryl, heteroaryl, and heterocyclyl, wherein each alkyl, heteroalkyl, cycloalkyl, alkenyl, alkynyl, aryl, heteroaryl, and heterocyclyl is further optionally substituted with 1-5 $R^g$, wherein n is 0, 1, or 2, and $R^a$, $R^b$, $R^c$, $R^d$, $R^e$, $R^f$ and $R^g$ are defined herein.

As used herein, the term "heteroalkyl," by itself or in combination with another term, means, unless otherwise stated, a stable straight or branched-chain alkyl group, preferably having from 2 to 14 carbons, more preferably 2 to 10 carbons in the chain, one or more of which has been replaced by a heteroatom selected from S, O, P and N, and wherein the nitrogen, phosphine, and sulfur atoms can optionally be oxidized and the nitrogen heteroatom can optionally be quaternized. The heteroatom(s) S, O, P and N may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—$S(O)_2$—$CH_3$, —O—$CH_3$, and —O—$CH_2$—$CH_3$. Similarly, the term "heteroalkylene" by itself or as part of another substituent means a divalent radical derived from heteroalkyl, as exemplified, but not limited by, —$CH_2$—$CH_2$—O—$CH_2$—$CH_2$— and —O—$CH_2$—$CH_2$—NH—$CH_2$—. For heteroalkylene groups, heteroatoms can also occupy either or both of the chain termini (e.g., alkyleneoxy, alkylenediamino, alkyleneamino, alkylenediamino, and the like). Still further, for alkylene and heteroalkylene linking groups, no orientation of the linking group is implied by the direction in which the formula of the linking group is written. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

As used herein, the term "optionally substituted heteroalkyl" or "optionally substituted heteroalkylene" as used herein by itself or as part of another group means the heteroalkyl or heteroalkylene as defined above is either unsubstituted or substituted with one or more (e.g., one, two, or three) substituents each independently chosen from, e.g., halo (e.g., F), oxo, nitro, cyano, $OR^a$, $CO_2R^a$, $OCO_2R^a$, $OSO_2NR^bR^c$, $SO_3R^a$, $OSO_3R^a$, $OS(O)_nR^e$, $NR^bR^c$, $C(=O)NR^bR^c$, $OC(=O)NR^bR^c$, $SO_2NR^bR^c$, $OC(=O)R^d$, $C(=O)R^d$, $S(O)_nR^e$, $C(=NR^f)NR^bR^c$, alkyl, heteroalkyl, cycloalkyl, alkenyl, alkynyl, aryl, heteroaryl, and heterocyclyl, wherein each alkyl, heteroalkyl, cycloalkyl, alkenyl, alkynyl, aryl, heteroaryl, and heterocyclyl is further optionally substituted with 1-5 $R^g$, wherein n is 0, 1, or 2, and $R^a$, $R^b$, $R^c$, $R^d$, $R^e$, $R^f$ and $R^g$ are defined herein.

As used herein, the term "haloalkyl" as used by itself or as part of another group refers to an alkyl substituted with one or more fluorine, chlorine, bromine and/or iodine atoms. In preferred embodiments, the haloalkyl is an alkyl group substituted with one, two, or three fluorine atoms. In one embodiment, the haloalkyl group is a $C_{1-10}$ haloalkyl group. In one embodiment, the haloalkyl group is a $C_{1-6}$ haloalkyl group. In one embodiment, the haloalkyl group is a $C_{1-4}$ haloalkyl group.

As used herein, the term "optionally substituted haloalkyl" as used by itself or as part of another group refers to an optionally substituted alkyl substituted with one or more fluorine, chlorine, bromine and/or iodine atoms.

As used herein, the term "alkoxy" as used by itself or as part of another group refers to a radical of the formula $OR^{a1}$, wherein $R^{a1}$ is an alkyl. As used herein, the term "optionally substituted alkoxy" refers to a radical of the formula $OR^{a1}$, wherein $R^{a1}$ is an optionally substituted alkyl.

As used herein, the term "cycloalkoxy" as used by itself or as part of another group refers to a radical of the formula $OR^{a1}$, wherein $R^{a1}$ is a cycloalkyl. As used herein, the term "optionally substituted cycloalkoxy" refers to a radical of the formula $OR^{a1}$, wherein $R^{a1}$ is an optionally substituted cycloalkyl.

As used herein, the term "aryl" as used by itself or as part of another group refers to a monocyclic, bicyclic or tricyclic aromatic ring system having from six to fourteen carbon atoms (i.e., $C_{6-14}$ aryl). As used herein, the term "arylene" as used by itself or as part of another group refers to a divalent radical derived from the aryl group defined herein. For example, a phenylene group includes two attaching points from the benzene ring, for example, 1,3-phenylene, 1,4-phenylene:

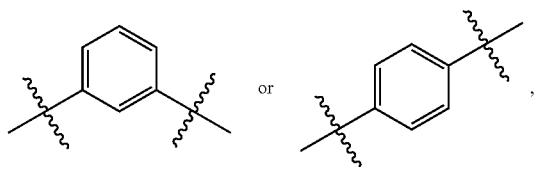 [SMILES: *c1cccc(*)c1 ; *c1ccc(*)cc1]

etc.

As used herein, the term "optionally substituted aryl" or "optionally substituted arylene" as used by itself or as part of another group means that the aryl or arylene as defined above is either unsubstituted or substituted with one to five substituents each independently chosen from, e.g., halo (e.g., F), nitro, cyano, $OR^a$, $CO_2R^a$, $OCO_2R^a$, $OSO_2NR^bR^c$, $SO_3R^a$, $OSO_3R^a$, $OS(O)_nR^e$, $NR^bR^c$, $C(=O)NR^bR^c$, $OC(=O)NR^bR^c$, $SO_2NR^bR^c$, $OC(=O)R^d$, $C(=O)R^d$, $S(O)_nR^e$, $C(=NR^f)NR^bR^c$, alkyl, heteroalkyl, cycloalkyl, alkenyl, alkynyl, aryl, heteroaryl, and heterocyclyl, wherein each alkyl, heteroalkyl, cycloalkyl, alkenyl, alkynyl, aryl, heteroaryl, and heterocyclyl is further optionally substituted with 1-5 $R^g$, wherein n is 0, 1, or 2, and $R^a$, $R^b$, $R^c$, $R^d$, $R^e$, $R^f$ and $R^g$ are defined herein; or two of the substituents are joined to form an optionally substituted cycloalkyl or optionally substituted heterocyclyl ring fused to the aryl.

As used herein, the term "heteroaryl" or "heteroaromatic" refers to monocyclic, bicyclic or tricyclic aromatic ring systems having 5 to 14 ring atoms (i.e., a 5- to 14-membered heteroaryl) and 1, 2, 3, or 4 heteroatoms independently chosen from oxygen, nitrogen and sulfur. In one embodiment, the heteroaryl has one heteroatom, e.g., one nitrogen. In another embodiment, the heteroaryl has 6 ring atoms, e.g., pyridyl. In one embodiment, the heteroaryl is a bicyclic heteroaryl having 8 to 10 ring atoms, e.g., a bicyclic heteroaryl having 1, 2, or 3 nitrogen ring atoms, such as quinolyl. As used herein, the term "heteroaryl" is also meant to include possible N-oxides. As used herein, the term "heteroarylene" as used by itself or as part of another group refers to a divalent radical derived from the heteroaryl group defined herein. For example, a pyridinylene group includes two attaching points from the pyridine ring, for example, 2,4-pyridinylene, 2,5-pyridinylene:

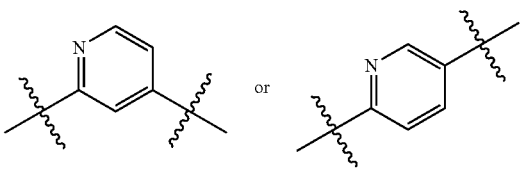

etc.

As used herein, the term "optionally substituted heteroaryl" or "optionally substituted heteroarylene" as used by itself or as part of another group means that the heteroaryl or heteroarylene as defined above is either unsubstituted or substituted with one or more (e.g., 1, 2, 3, 4, or 5) substituents each independently chosen from, e.g., halo (e.g., F), nitro, cyano, $OR^a$, $CO_2R^a$, $OCO_2R^a$, $OSO_2NR^bR^c$, $SO_3R^a$, $OSO_3R^a$, $OS(O)_nR^e$, $NR^bR^c$, $C(=O)NR^bR^c$, $OC(=O)NR^bR^c$, $SO_2NR^bR^c$, $OC(=O)R^d$, $C(=O)R^d$, $S(O)_nR^e$, $C(=NR^f)NR^bR^c$, alkyl, heteroalkyl, cycloalkyl, alkenyl, alkynyl, aryl, heteroaryl, and heterocyclyl, wherein each alkyl, heteroalkyl, cycloalkyl, alkenyl, alkynyl, aryl, heteroaryl, and heterocyclyl is further optionally substituted with 1-5 $R^g$, wherein n is 0, 1, or 2, and $R^a$, $R^b$, $R^c$, $R^d$, $R^e$, $R^f$ and $R^g$ are defined herein; or two of the substituents are joined to form an optionally substituted cycloalkyl or optionally substituted heterocyclyl ring fused to the heteroaryl.

As used herein, the term "heterocycle" or "heterocyclyl" as used by itself or as part of another group refers to saturated and partially unsaturated (e.g., containing one or two double bonds) cyclic groups containing one, two, or three rings having from three to fourteen ring members (i.e., a 3- to 14-membered heterocycle) and at least one heteroatom. Each heteroatom is independently selected from the group consisting of oxygen, sulfur, including sulfoxide and sulfone, and/or nitrogen atoms, which can be quaternized. The term "heterocyclyl" is meant to include cyclic ureido groups such as imidazolidinyl-2-one, cyclic amide groups such as β-lactam, γ-lactam, δ-lactam and ε-lactam, and cyclic carbamate groups such as oxazolidinyl-2-one. In one embodiment, the heterocyclyl group is a 4-, 5-, 6-, 7- or 8-membered cyclic group containing one ring and one or two oxygen and/or nitrogen atoms. As used herein, the term "heterocyclylene" as used by itself or as part of another group refers to a divalent radical derived from the heterocyclyl group defined herein. For example, a piperidinylene group includes two attaching points from the piperidine ring:

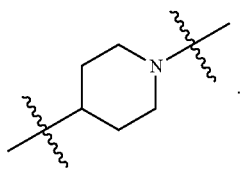 [SMILES: *C1CCN(*)CC1]

The heterocyclyl or heterocyclylene can be optionally linked to the rest of the molecule through a carbon or nitrogen atom.

As used herein, the term "optionally substituted heterocyclyl" or "optionally substituted heterocyclylene" as used herein by itself or part of another group means the heterocyclyl or heterocyclylene as defined above is either unsubstituted or substituted with one or more (e.g., 1, 2, 3, 4, or 5) substituents each independently chosen from, e.g., halo (e.g., F), oxo, nitro, cyano, $OR^a$, $CO_2R^a$, $OCO_2R^a$, $OSO_2NR^bR^c$, $SO_3R^a$, $OSO_3R^a$, $OS(O)_nR^e$, $NR^bR^c$, $C(=O)NR^bR^c$, $OC(=O)NR^bR^c$, $SO_2NR^bR^c$, $OC(=O)R^d$, $C(=O)R^d$, $S(O)_nR^e$, $C(=NR^f)NR^bR^c$, alkyl, heteroalkyl, cycloalkyl, alkenyl, alkynyl, aryl, heteroaryl, and heterocyclyl, wherein each alkyl, heteroalkyl, cycloalkyl, alkenyl, alkynyl, aryl, heteroaryl, and heterocyclyl is further optionally substituted with 1-5 $R^g$, wherein n is 0, 1, or 2, and $R^a$, $R^b$, $R^c$, $R^d$, $R^e$, $R^f$ and $R^g$ are defined herein; or two of the substituents are joined to form an optionally substituted aryl or optionally substituted heteroaryl ring fused to the heterocyclyl or heterocyclylene. Substitution may occur on any available carbon or nitrogen atom, and may form a spirocycle.

As used herein, the term "salt" includes both internal salt and external salt. In some embodiments, the salt is an internal salt, i.e., containing a zwitterion structure. In some embodiments, the salt is an external salt. In some embodiments, the external salt is a pharmaceutically acceptable salt having a suitable counter ion. Suitable counterions for pharmaceutical use are known in the art.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound described herein to a subject in need of such treatment.

The term "inhibition", "inhibiting", "inhibit," or "inhibitor" refer to the ability of a compound to reduce, slow, halt or prevent activity of a particular biological process (e.g., TGF beta-1 mediated signaling in a cell relative to vehicle).

The term "subject" (alternatively referred to herein as "patient") as used herein, refers to an animal, preferably a mammal, most preferably a human, who has been the object of treatment, observation or experiment.

Conjugates of the present disclosure may contain asymmetrically substituted carbon atoms in the R or S configuration. Compounds having asymmetrically substituted carbon atoms with equal amounts of R and S configurations are racemic at those carbon atoms. Atoms with an excess of one configuration over the other are assigned the configuration present in the higher amount, preferably an excess of about 85%-90%, more preferably an excess of about 95%-99%, and still more preferably an excess greater than about 99%. Accordingly, this invention includes racemic mixtures, relative and absolute stereoisomers, and mixtures of relative and absolute stereoisomers.

Conjugates of the present disclosure can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to $^2H$, $^3H$, $^{13}C$, $^{14}C$, $^{15}N$, $^{32}P$, $^{35}S$, $^{18}F$, $^{36}Cl$, and $^{125}I$. Compounds that contain other isotopes of these and/or other atoms are within the scope of this invention.

Unless expressly stated to the contrary, combinations of substituents and/or variables are allowable only if such combinations are chemically allowed and result in a stable compound. A "stable" compound is a compound that can be prepared and isolated and whose structure and properties remain or can be caused to remain essentially unchanged for a period of time sufficient to allow use of the compound for the purposes described herein (e.g., therapeutic administration to a subject).

EXAMPLES

The various starting materials, intermediates, and compounds of the preferred embodiments can be isolated and purified where appropriate using conventional techniques such as precipitation, filtration, crystallization, evaporation, distillation, and chromatography. Characterization of these compounds can be performed using conventional methods such as by melting point, mass spectrum, nuclear magnetic resonance, and various other spectroscopic analyses. Exemplary embodiments of steps for performing the synthesis of products described herein are described in greater detail infra.

Example 1. Synthesis of Compound 1: (1-hydroxy-4-(((2-((4-(2-(pyridin-2-yl)-5,6-dihydro-4H-pyrrolo[1,2-b]pyrazol-3-yl)quinolin-7-yl)oxy)ethoxy)carbonyl)amino)butane-1,1-diyl)bis(phosphonic acid)
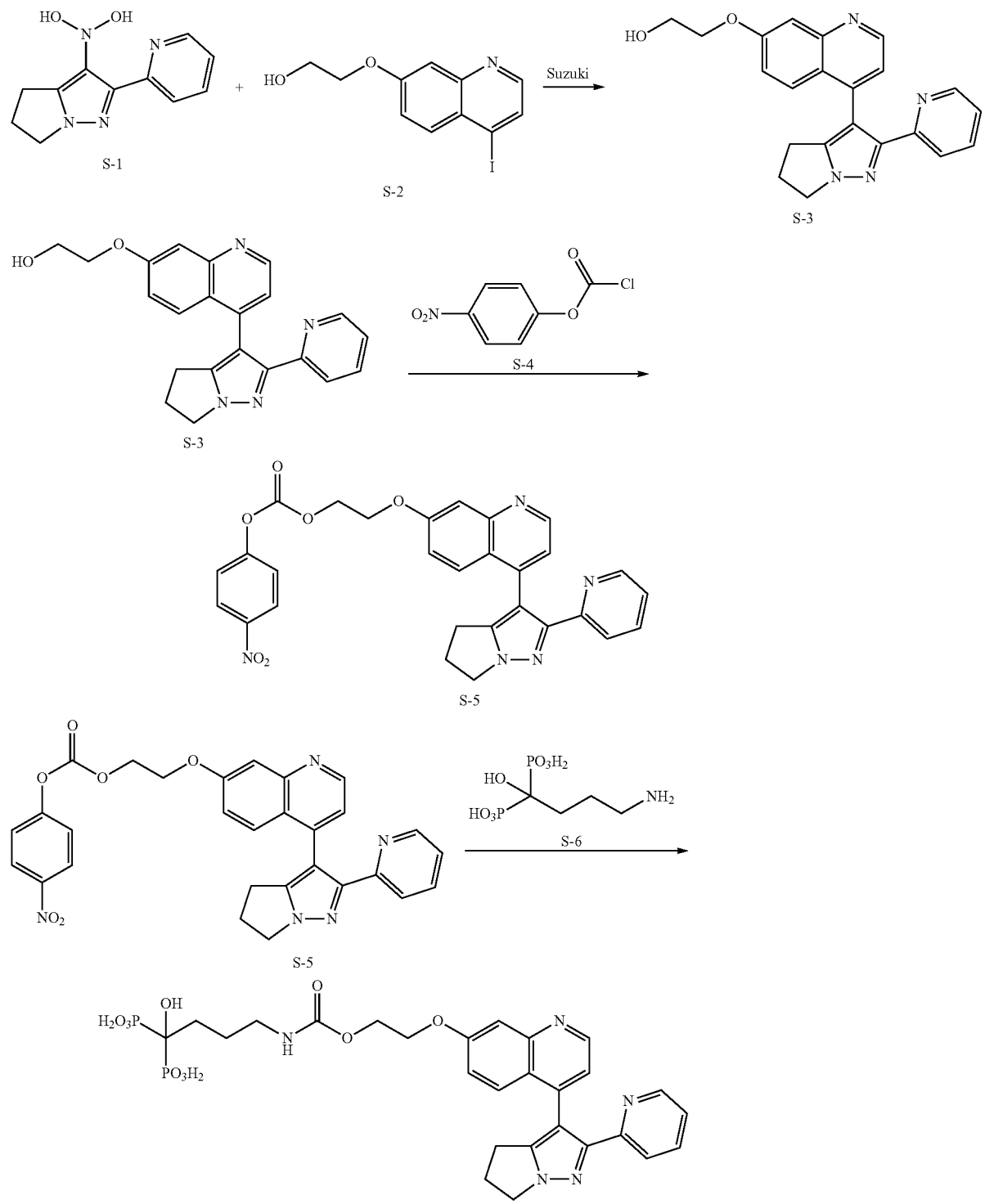

Step 1. Compound S-3 is a known compound as described in U.S. Pat. No. 7,265,225, which can be alternatively prepared as follows. A 250 mL-oven-dried three-necked flask under inert atmosphere of nitrogen was charged with NaOH (3.2 g, 79.35 mmol), S-2 (5 g, 15.87 mmol, 1 eq.), water (10 mL) and 1,4-dioxane (50 mL). After the mixture was heated to 80° C., S-1 (4.4 g, 19.05 mmol, 1.2 eq.) in 1,4-dioxane (50 mL) was added dropwise at 80° C. by constant pressure dropping funnel over 1 h. The resulting mixture was stirred at 80° C. until the HPLC showed the compound S-2 was disappeared (about 2 h). The mixture was filter through a thin pad of celite at this time. The filtrate was allowed to reach room temperature and concentrated to remove the solvent then get a yellow residue. The residue was diluted with water (50 mL) and stirred overnight, filtered and dried to get a yellow solid. The yellow solid was recrystallized with ethanol to get a white solid 5.02 g (yield 85%). $^1$H NMR (400 MHz, CDCl$_3$) δ 8.79 (d, J=4.8 Hz, 1H), 8.43 (d, J=4.0 Hz 1H), 7.67 (d, J=9.2 Hz 1H), 7.46 (d, J=2.4 Hz 1H), 7.43 (td, J=1.6 Hz, J=7.6 Hz, 1H), 7.24 (d, J=8 Hz 1H), 7.18 (d, J=4.4 Hz 1H), 7.07-7.03 (m, 2H), 4.38 (t, J=7.6 Hz 2H), 4.26 (t, J=4.4 Hz 2H), 4.05 (t, J=4.4 Hz 2H), 2.86 (t, J=6.8 Hz 2H), 2.73-2.66 (m, 2H), 2.16 (s, 1H). MS (m/z): Calcd. for C$_{22}$H$_{20}$N$_4$O$_2$ [M+H]$^+$ 373.1. found 373.2.

Step 2. To a mixture of S-3 (10 g, 26.9 mmol, 1 eq.), dry triethylamine (13.57 g, 134.4 mmol, 5 eq.) and dry dichloromethane (100 mL) was added S-4 (10.83 g, 53.7 mmol, 2 eq.) in the dry dichloromethane (100 mL) at 0° C. under N$_2$. The mixture was kept at 8° C. and stirred until the HPLC showed S-3 was consumed completely. The mixture was washed with 18.3% sodium dihydrogen phosphate aqueous solution (150 mL). The water phase was extracted with CH$_2$Cl$_2$ (100 mL). The combined organic phase was successively washed with 18.3% sodium dihydrogen phosphate aqueous solution (150 mL), water (150 mL) and saturated brine (150 mL) twice and dried with Na$_2$SO$_4$. The dried organic phase was concentrated to get a yellow solid. The yellow solid was diluted with ethyl acetate (20 mL) and methyl tert-butyl ether (80 mL) and stirred at 40° C. for 1 h. The result mixture was cooled to 0° C., stirred for 1 h, and filtered to get a white solid 13.3 g (yield 92.12%). $^1$H NMR (400 MHz, CDCl$_3$) δ 8.81 (d, J=4.4 Hz, 1H), 8.42 (d, J=4.4 Hz, 1H), 8.30-8.27 (m, 2H), 7.69 (d, J=9.2 Hz, 1H), 7.46-7.39 (m, 4H), 7.26 (d, J=5.2 Hz, 1H), 7.21 (d, J=4.8 Hz, 1H), 7.08-7.05 (m, 2H), 4.73-4.70 (m, 2H), 4.45-4.43 (m, 2H), 4.38 (t, J=7.2 Hz, 2H), 2.87 (t, J=6.8 Hz, 2H), 2.74-2.2.67 (m, 2H). MS (m/z): Calcd. for C$_{29}$H$_{24}$N$_5$O$_6$ [M+H]$^+$ 538.17. found 538.2.

Step 3. A solution of S-5 (1 g, 1.86 mmol, 1.2 eq.) was treated with a solution of S-6 (0.5036 g, 1.55 mmol, 1 eq.) dissolved in the mixed solvent of triethylamine (0.94 g, 9.3 mmol, 6 eq.), H$_2$O (6 mL) and 1,4-dioxane (2 mL) under N$_2$. The resulting yellow mixture was stirred at 25° C. until $^{31}$P NMR showed S-6 was disappeared, then the mixture was treated with acetic acid (0.93 g, 15.5 mmol, 10 eq.) and sodium acetate (0.636 g, 7.76 mmol, 5 eq.) and heated to 80° C. After added methanol (30 mL), the mixture was stirred for 1 h at 80° C. and cooled to 0° C. to resultant precipitate. The precipitate was collected by filtration, and washed with methanol to get Compound 1 a white solid (1 g, yield 93.1%)$^1$H NMR (400 MHz, D$_2$O+Na$_2$CO$_3$) δ 8.42 (d, J=4.8 Hz, 1H), 8.03 (d, J=4.0 Hz, 1H), 7.44 (t, J=6.8 Hz, 1H), 7.156-7.133 (m, 2H), 7.07-7.04 (m, 2H), 6.91 (d, J=4.4 Hz, 1H), 6.65 (d, J=9.6 Hz, 1H), 4.27 (s, 2H), 4.16 (s, 2H), 4.10 (s, 2H), 3.05 (t, J=6.8 Hz, 2H), 2.41 (s, 4H), 1.79-1.65 (m, 4H). $^{31}$P NMR (163 MHz, D$_2$O+Na$_2$CO$_3$) δ 18.64. MS (m/z): Calcd. for C$_{29}$H$_{24}$N$_5$O$_6$P$_2$ [M+H]$^+$ 648.16. found 648.2.

Example 2. Synthesis of Compound 2

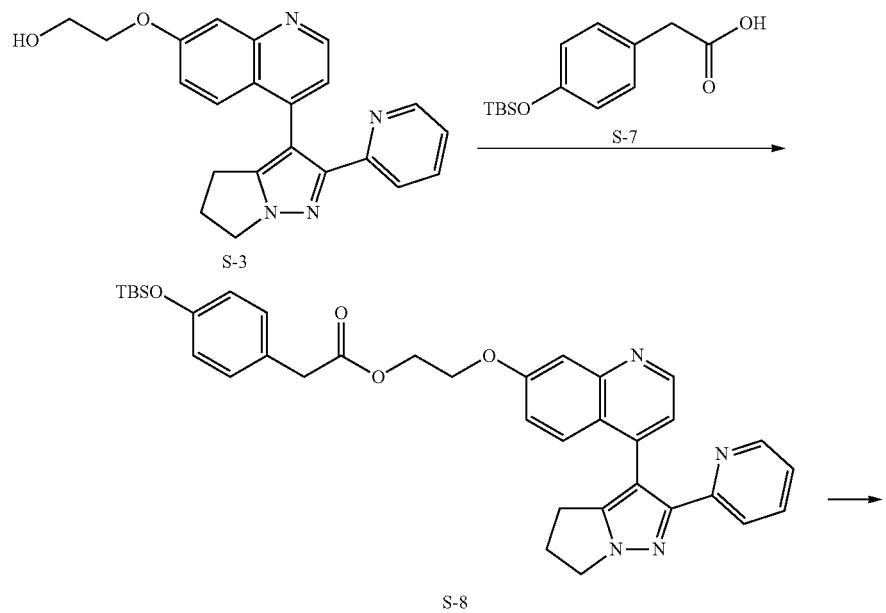

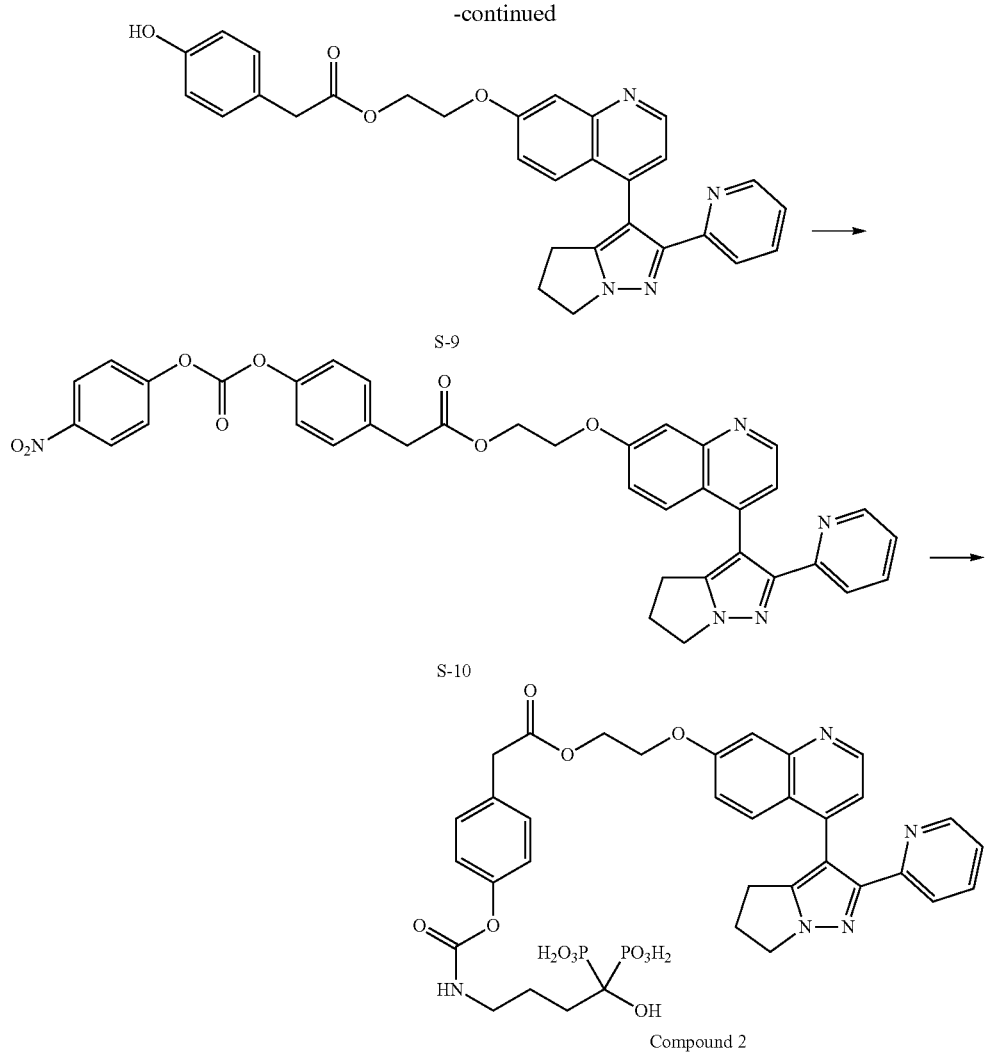

Step 1. To a solution of p-hydroxyphenylacetic acid (10.0 g, 65.7 mmol) in THF (80 mL) were successively added imidazole (22.4 g, 329 mmol) and TBSCl (27.7 g, 184 mmol) at 0° C., and the mixture was stirred for an hour while elevating to room temperature. To this mixture was added a solution of saturated Na$_2$CO$_3$ (250 ml) and the mixture was stirred at room temperature for another hour. Then added 2 M HCl aqueous solution (650 ml) and the product was extracted with ethyl acetate (300 mL×3). The combined organic extract was washed successively with water (400 ml) and brine (300 ml), followed by drying over anhydrous sodium sulfate. After filtration and concentration under reduced pressure, the residue was purified by column chromatography (silica gel 200 g, n-hexane, n-hexane/ethyl acetate/acetic acid=1/1/0.05) to give Compound S-7 as colorless solid, yield (10.6 g, 39.9 mmol, 60.7%). $^1$H NMR (400 MHz, CDCl$_3$) δ 7.13 (d, J=8.4 Hz, 2H), 6.79 (d, J=8.4 Hz, 2H), 3.57 (s, 2H), 0.97 (s, 9H), 0.17 (s, 6H).

Step 2. The mixture of S-3 (3.0 g, 8 mmol), DCC (2.48 g, 12 mmol, 1.5 eq), pyridine (1.26 g, 16 mmol, 2.0 eq), 2-(4-((tert-butyldimethylsilyl)oxy)phenyl)acetic acid (2.56 g, 9.6 mmol, 1.2 eq), DMAP (0.1 g) in 15 ml DMF was stirred overnight at room temperature under N$_2$, the reaction was quenched by 100 ml water and extracted by EA. The organic phase was dried with MgSO$_4$, filtered and concentrated to give a residual oil which was purified by flash column chromatography on silica gel (EA) to afford the compound S-8 (4.1 g) as a white solid. $^1$H NMR (400 MHz, CDCl$_3$) δ 8.79 (d, J=4.5 Hz, 1H), 8.43 (d, J=4.1 Hz, 1H), 7.66 (d, J=9.2 Hz, 1H), 7.44-7.40 (m, 2H), 7.22 (d, J=8.0 Hz, 1H), 7.18 (d, J=4.5 Hz, 1H), 7.13 (d, J=8.4 Hz, 2H), 7.07-7.02 (m, 2H), 6.76 (d, J=8.5 Hz, 2H), 4.51 (t, J=4.6 Hz, 2H), 4.37-4.31 (m, 4H), 3.60 (s, 2H), 2.88-2.83 (m, 2H), 2.73-2.68 (m, 2H), 0.96 (s, 9H), 0.17 (s, 6H).

Step 3. 4.1 g compound S-8 was dissolved in 20 ml THF, and 4 ml 1M HF in pyridine was added. The mixture was stirred for 2 h, concentrated, 20 ml water was added to the residual and extracted with EA three times, then the aqueous phase was neutralized with Et$_3$N and extracted by EA. The second EA phase was dried with MgSO$_4$, filtered and concentrated to afford the compound S-9 (1.6 g) as a white foam solid. $^1$H NMR (400 MHz, CDCl$_3$) δ 8.66 (d, J=4.6 Hz, 1H), 8.30 (t, J=2.3 Hz, 1H), 7.69-7.64 (m, 3H), 7.26 (d, J=2.6 Hz, 1H), 7.18-7.15 (m, 1H), 6.88 (d, J=4.5 Hz, 1H), 6.84-6.80

(m, 3H), 6.55 (d, J=8.5 Hz, 2H), 4.44 (s, 2H), 4.34-4.31 (m, 4H), 3.45 (s, 2H), 2.79 (bs, 2H), 2.69-2.66 (m, 2H).

Step 4. A solution of compound S-9 (405 mg, 0.8 mmol) in dry $CH_3CN$ (10 ml) was treated with triethylamine (242.4 mg, 2.4 mmol, 3.0 eq) under argon atmosphere, the mixture was stirred for 15 min at room temperature. Then 4-nitrophenyl chloroformate (241.2 mg, 1.2 mmol, 1.5 eq) in dry $CH_3CN$ was added dropwisely. The final mixture was stirred at room temperature for 3 h, after that it was concentrated to give a residual oil which was washed by 5 ml dry ether twice to afford crude S-10 as a light yellow solid, which is used for next step without further purifying.

Step 5. A solution of alendronic acid (160 mg, 0.64 mmol, 0.8 eq) and triethylamine (323.2 mg, 3.2 mmol, 4.0 eq) dissolved in $H_2O$ (10 mL) was treated with a solution of S-10 in dioxane (10 mL). The resulting yellow mixture was stirred at room temperature and monitored by TLC. After the S-10 was complete consumed, the solution was concentrated and diluted with $EtOAc/H_2O$ (1:1, 20 ml). The layers were separated and the aqueous phase was extracted with EtOAc (3×10 ml). The remaining aqueous solution was concentrated to afford crude product as a yellow solid. The crude product was then dissolved in the minimal amount of $H_2O$, and to this solution was added a solution of 0.5 M sodium acetate in MeOH. The resultant precipitate was collected by filtration, and washed with $EtOH/H_2O$ (9:1, 3.0 ml), EtOH (3.0 ml) and $Et_2O$ to give the crude product which was prepared by LC to afford Compound 2 160 mg as a white powder. $^1H$ NMR (400 MHz, $D_2O$) δ 8.56 (s, 1H), 8.04 (s, 1H), 7.44 (s, 1H), 7.22-7.17 (m, 3H), 7.11 (d, J=2.8 Hz, 1H), 7.03 (s, 1H), 6.92 (d, J=8.2 Hz, 2H), 6.71 (d, J=8.2 Hz, 2H), 6.57 (d, J=7.9 Hz, 1H), 4.37 (s, 2H), 4.20 (s, 4H), 3.44 (s, 2H), 3.11 (s, 2H), 2.48 (bs, 4H), 1.92-1.79 (m, 4H). $^{31}P$ NMR (163 MHz, $D_2O$) δ 18.27. MS (m/z): Calcd. for $C_{35}H_{37}N_5O_{12}P_2[M+H]^+$ 782.19. found 782.1.

Biological Example 1. In Vitro and In Vivo TGF Beta Inhibition for Treating CED General Methods and Material All transgenic animals used in this study are as described in the Animals section. To characterize the efficacy of conjugate in CED animal model, male transgenic animals of 4-weeks of age received conjugate intraperitoneal injection (50 µg/kg, 100 µg/kg and 1 mg/kg) once a week for 8 weeks before sacrifice. During cell counting, microCT analysis and histological staining analysis, all manual quantification is performed in a blind manner to eliminate observer bias. Animals were randomly assigned to groups for experiments in CED animal studies.

Mice: According to Tang et al., *Nat Med.* 15:757-765 (2009), a mutation in the coding area of the TGF-β1 latency protein was generated in mice, and the active form of TGF-β1 was secreted by osteoblasts. Mice were divided into four groups (n=6 per group): Littermate (wild-type) (treated with 100 µl PBS), CED (treated with 100 µl PBS), ALN (CED mice treated with 100 µg/kg alendronate in 100 µl PBS), and Compound 1 (CED mice treated with 100 µg/kg conjugate in 100 µl PBS). All mice received the intraperitoneal injections once a week for 2 months, beginning at 1 month of age until sacrifice at 3 months of age. The tibias of the mice were collected and analyzed.

Cell culture: HeLa cells and BMSCs from mice were cultured in Dulbecco's Modified Eagle's Medium (GIBCO) supplemented with 10% fetal bovine serum (FBS; Sigma), 100 units/ml penicillin, 100 µg/ml streptomycin (Sigma), and 2 mM glutamine and were incubated at 37° C. in a humidified chamber supplemented with 5% CO2. Cultured cells were treated with DMSO, alendronate (referred to as ALN in this Example and related Figures, 10 M), and Compound S-3 (referred to as Inhibitor in this Example and related Figures, 10 µM) for 1 h or Compound 1 (referred to as Conjugate in this Example and related Figures, 10 µM) for 1 h, 24 h, and 48 h. Cells were then exposed to 5 ng/ml of recombinant human TGF-β1 (R&D Systems) for 30 min and processed for cell staining and Western blotting.

Cell staining: BMSCs were washed 3 times with PBS and fixed by 4% paraformaldehyde (PFA) for 30 min. Cells were then washed 3 times with PBS and incubated with 3% BSA, 0.1% Triton in PBS for 1 h. Samples were incubated with pSmad2/3 antibodies (Santa Cruz Biotechnology Inc., 1:50, sc-11769) overnight at 4° C. Secondary antibodies conjugated with fluorescence were added, and plates were incubated at room temperature for 1 h while avoiding light. Cells were counted under the microscope (Olympus DP71).

Western blot: HeLa cells were lysed with Protease Inhibitor Cocktail and Protease Inhibitor Cocktail (Roche), and mixed with an equal volume of 2×SDS-PAGE sample buffer with DTT. Samples were boiled and cleared by centrifuge, separated by SDS-PAGE, and transferred onto nitrocellulose (NC) membranes. Membranes were blocked with 5% non-fat dry milk and incubated with primary antibodies at 4° C. overnight. Primary antibodies include rabbit anti-Smad2 antibody (Cell Signaling Technology, 3122, 1:1,000) and rabbit anti-Phospho-Smad2 (Ser465/467) antibody (Cell Signaling Technology, 3108, 1:1,000). HRP-conjugated goat anti-rabbit IgG (Santa Cruz Biotechnology, 2054, 1:5,000) was used as secondary antibody. Signals were detected with Super Signal West Dura Extended Duration Substrate (Thermo Scientific).

Microcomputed tomography analysis: Tibia collected from mice were dissected to remove soft tissue, fixed overnight in 70% ethanol, and analyzed with a high-resolution microcomputed tomography (µCT) imaging system (MicroCT40; Scanco Medical AG, Basserdorf, Switzerland). The scanner was set at a voltage of 55 kVp and a current of 109 µA. The resulting two-dimensional longitude-sectional images or three-dimensional whole-bone images are shown in gray scale. Three-dimensional structural parameters, total bone volume per tissue volume, cortical bone volume, cortical bone thickness, and cortical bone porosity were given.

Histochemistry, immunohistochemistry, and immunofluorescence: At the time of euthanasia, tibias were collected and fixed in 10% buffered formalin for 48 h, decalcified in 10% EDTA (pH 7.4) for 14 d, and then embedded in paraffin. Tartrate-resistant acid phosphatase (Trap) staining was performed using a standard protocol (Sigma-Aldrich, 387A-1KT). Immunostaining was performed using a standard protocol. Sections were incubated with primary antibodies to mouse pSmad2/3 (Santa Cruz Biotechnology Inc., 1:50, sc-11769) and osteocalcin (Takara Bio Inc., 1:200, M137) overnight at 4° C. For immunohistochemical staining, a liquid Diaminobenzidine (DAB)+Chromogen System (Dako, K3468) was used to detect immunoreactivity, followed by counterstaining with hematoxylin and eosin (Sigma-Aldrich, MHS16).

Immunofluorescence staining was performed using as described. Osterix (Abcam, 1:600, ab22552), Collagen I (Abcam, 1:500, ab21286), pSmad2/3 (Santa Cruz Biotechnology Inc., 1:50, sc-11769), CD31 (Abcam, 1:100, ab28364), Endomucin (Santa Cruz Biotechnology Inc., 1:100, sc-19900), and Leptin Receptor (R&D, 1:100, AF497) 11 were incubated overnight at 4° C. Secondary antibodies conjugated with fluorescence were added, and slides were incubated at room temperature for 1 h while avoiding light. Sections were microphotographed to perform histomorphometric measurements (Olympus DP71). The quantitative histomorphometric analysis was conducted in a blinded fashion with OsteoMeasureXP Software (OsteoMetrics, Inc.). The number of positively stained cells in the whole tibia subchondral bone area per specimen was counted in five sequential sections per mouse in each group.

Flow cytometry: Bone marrow cells in the distal one-third of tibia were collected from each group (n=6) after 2 months of conjugate treatment. Red blood cells were lysed in commercial ACK lysis buffer (Quality Biological, Inc., 118-156-101). After centrifugation (1,200 r.p.m. for 5 min at room temperature), cell pellets were resuspended and fixed in 4% PFA. Cells were then washed with 0.1% BSA in PBS and counted. One million cells per milliliter were permeabilized in 0.1% Triton X-100 before blocking in 3% FACS buffer (PBS, 3% FBS, and 0.1% NaN3 sodium azide) for 30 min on ice. Cells were incubated with endomucin antibody (Santa Cruz, sc-65495), Leptin Receptor (R&D, 1:100, AF497), or isotype control antibody for 1 h at 37° C. in a dark room and then washed twice with 0.1% BSA in PBS. After washing, cells were stained with APC-conjugated CD31 antibody (R&D Systems, FAB3628A) for 45 min. Cells were acquired immediately after washing with 3% FACS buffer. Probes were analyzed using a FACS Calibur flow cytometer and CellQuest software (Becton Dickinson).

Statistical Methods: Data are presented as the mean±s.d. Comparisons for all data among different groups were performed using multifactorial ANOVA. The level of significance was set at $P<0.05$. All data analyses were performed using SPSS 15.0 analysis software (SPSS Inc).

Results and Discussions

Cells incubated with the conjugate Compound 1, were performed both Western blotting and immunofluorescence staining for phosphorylation of Smad2/3 (pSmad2/3). It was confirmed that incubation with Compound 1 significantly reduced the number of pSmad2/3-positive cells and the expression level of pSmad2 in a time dependent manner. This confirms that the conjugates of the present disclosure such as Compound 1 can release a TGF beta inhibitor. See FIG. 1.

Compound 1 was also tested for tissue distribution following intraperitoneal injection. Survival analysis of wild-type mice treated with the conjugate or PBS (negative control) revealed that doses below 5 mg/kg per week via intraperitoneal administration were safe; no mice death was found under 50 µg/kg, 100 µg/kg, and 1 mg/kg group. See FIG. 1, (F). It was then determined whether the conjugate delivered TβR1I (TGF-beta type 1 receptor inhibitor) specifically to bone and hydrolyzed over time (intraperitoneal injection, DMSO, 100 µg/kg of ALN, Inhibitor, or Conjugate).

It was confirmed that Compound 1 was delivered to the bone and inhibited TGF beta 1 mediated signaling in mice. Specifically, pSmad2/3 stainings of Compound 1 treated mice suggested the TGF-β1 signaling in tibias was inhibited in a time-dependent manner in vivo. In contrast, Compound S-3 (see Example 1) treated mice did not show significant differences in inhibiting TGF-β1 signaling compared with a vehicle control group. Further, the hematoxylin and eosin (HE) staining and pSmad2/3 staining of heart, liver, lung, and kidney demonstrated normal tissue structures and TGF-β1 activation. (FIG. 6) Thus, the conjugates of the present disclosure such as Compound 1 can be selectively delivered to the bone and slowly releases TGF beta inhibitor. See FIG. 1, (G) and (H).

Mice were also intraperitoneally injected with the conjugates (Compound 1) once a week for 8 weeks (data of 100 µg/kg per week group is presented as Conjugate). After 8-week treatment, a µCT three-dimensional reconstruction of the tibia showed that the bone morphology of Conjugate-treated mice was significantly improved compared with CED and ALN-treated mice (FIG. 2, (A)). The bone fracture incidence was 8.3% in Conjugate-treated mice, 58.3% in CED mice, and 50% in ALN-treated mice, indicating that conjugate treatment significantly reduced bone fractures (FIG. 2, (B)).

After conjugate treatment, the total bone volume/tissue volume (BV/TV) distribution in Conjugate group was restored, while the total BV/TV in CED and ALN groups still demonstrated unregulated states. The total BV/TV showed no significant difference among all groups (FIG. 2, (C) and (D)). These data demonstrate that the conjugate rescues CED mice from uncoupled bone remodeling.

Studies reported that the most common symptom in CED patients is cortical bone thickening. After 8-week conjugate treatment, fluctuating changes in the cortical bone parameters was found in CED and ALN group. The total cortical bone volume was decreased, and the bone porosity rate and cortical bone thickness were significantly increased in CED and ALN group, suggesting poor cortical bone quality. On the other hand, the cortical bone parameters in Conjugate group show no significant difference compared with Littermate group (FIG. 2, (E)-(H)). These results demonstrated that the conjugate effectively restored normal cortical bone quality in CED mice.

Tang Y. et al. has shown that intraperitoneal injection of a TGF beta inhibitor (SB505124) rescued bone remodeling defects in CED mice with less tibial fractures and with significantly reduced cortical thickness, porosity, osteoblasts surface and osteoclasts surfaces. *Nat Med.* 15:757-765 (2009). Test has shown that intraperitoneal injection of Compound 1 in CED mice showed similar efficacy at a much lower dose.

To determine if the conjugate inhibited TGF-β1 signaling pathway in vivo, the histological analysis was performed. The pSmad2/3 staining clearly showed that pSmad2/3 positive cells were significantly decreased in Conjugate group compared with CED group and ALN group, suggesting that the conjugate effectively inhibited TGF-β1 signaling (FIG. 3, (B) and (C)).

To explore whether the conjugate restored normal bone remodeling, the Hematoxylin and Eosin (HE) staining was performed to detect bone formation, and tartrate-resistant acid phosphatase (TRAP) and Osteocalcin (Ocn) co-staining to observe bone remodeling in diaphysis. The HE staining showed aberrant bone formation was found the diaphysis bone marrow CED and ALN group compared with Conjugate group and Littermate group (FIG. 3, (A)). The TRAP and Ocn co-staining also demonstrated the same prevalence, suggesting that bone remodeling in CED occurred in an incorrect spatial manner (FIGS. 3 (D)-(F)). After conjugate treatment, the number of TRAP+ and Ocn+ cells was decreased. Taken together, these data clearly show that the conjugate restored normal bone remodeling of CED mice via inhibiting TGF-β1 signaling pathway.

Studies demonstrated that TGF-β1 had no direct influence on osteogenesis; however, the aberrantly highly active bone formation in CED suggested TGF-β1 regulates osteogenesis in an unknown mechanism. Recently, CD31+Emcn+ double positive vessels were reported to couple osteogenesis and angiogenesis, and TGF-β1 regulates vessel formation. Therefore, it was hypothesized that TGF-β1 may regulate CD31+Emcn+ double positive vessels formation. Fluorescence activated cell sorting (FACS) and immune-fluorescent staining was carried out to verify this hypothesis. FACS of tibia bone marrow showed that CD31+Emcn+ double positive cells were highly increased in CED group and ALN group; while, conjugate treatment significantly reduced the number of double positive cells. Next, the immunofluorescence staining was performed to detect vessels formation, results suggested that the CD31+Emcn+ vessel surfaces were highly increased in CED group and ALN group, and conjugate treatment rescued abnormal vessel formation.

Then, whether TGF-β1 drove vessel formation contributed to highly proosteogenic microenvironment was explored, and the co-staining of Ocn, Osx, and Col1 with Emcn was performed. The results suggested that the number of Ocn+, Osx+, and Col1+ cells in CED group and ALN group were significantly increased compared with Littermate group, and most of the staining positive cells located perivascularly (less than 20 m from vascular). While in Conjugate group, the number of Ocn+, Osx+, and Col1+ cell showed no significant difference compared with Littermate group, and most of the cells located on the bone surface. These results suggested that TGF-β1 induced CD31+Emcn+ double positive vessels formation to provide an aberrant pro-osteogenic microenvironment. See e.g., FIG. 5.

In previous studies, it was reported that TGF-β1 guided MSCs to migrate to the bone resorption sites; while, the exact mechanism remained unclear. Recent studies pointed out that Leptin receptor positive (LepR+) BMSC migrated to bone trauma sites and contributed the most bone formation in adult mice. Therefore, FACS and immunofluorescent staining was performed to verify whether TGF-β1 recruited LepR+BMSCs during aberrant bone remodeling. The FACS suggested that the number of LepR+ cells was significantly increased in CED group and ALN group (FIG. 4, (E)). Next, LepR and pSmad2/3 was co-stained to explore whether the TGF-β1 signaling pathway was activated in recruited LepR+ BMSCs 12 (FIG. 4, (F) and (G)). Immunofluorescence staining revealed LepR+pSmad2/3+ dual positive BMSC were significantly increased in CED group and ALN group. After conjugate treatment, both LepR+ cells in bone marrow and LepR+pSmad2/3+ dual positive BMSC were significantly decreased, demonstrating that TGF-β1 recruited LepR+ cells in aberrant bone remodeling.

Previous studies demonstrated that TGF-β1 recruits BMSCs to bone resorption sites, but it is not known what type of BMSCs was recruited. LepR$^+$ cells are the major BMSCs committed to osteoblastic lineage differentiation during adult bone formation. After injury in bone, LepR$^+$ cells are activated, recruited to the trauma site, and committed to osteoblastic lineage differentiation. It was found that LepR$^+$ cells were recruited during aberrant bone remodeling. During CED progression, the number of LepR$^+$ cells was significantly increased, and TGF-β1 was highly activated. Importantly, conjugate treatment decreased both the number of LepR$^+$ cells and the level of TGF-β1, further supporting that TGF-β recruits LepR$^+$ cells during bone remodeling.

The differentiation of LepR$^+$ cells is regulated by the local microenvironment. The inhibited osteogenesis in Conjugate-treated mice suggested that TGF-β1 modulated the local microenvironment by stimulating formation of type H vessels. Normally, type H vessels locate in the metaphysis and cortical bone, and their number gradually decreases during aging. In CED mice, type H vessels were highly expressed in the bone marrow compared with the normal distribution seen in the bone metaphysis, suggesting an incorrect spatial distribution. According to a study by Kusumbe et al., the number of type H vessels diminishes with age; however, the vessel surface remained high in 3-month-old CED mice compared with littermate mice, demonstrating incorrect temporal expression in CED mice. The results showed that Osx$^+$ and Col1α$^+$ cells attached to vessels, indicating that type H vessels provide a highly pro-osteogenic microenvironment to induce osteoblastic differentiation. Ocn$^+$ cells in CED mice were distributed in bone marrow rather than along the cortical bone, as in Littermate mice, indicating that mature osteoblasts were highly activated in bone marrow and disrupted bone formation. Conjugate treatment significantly decreased type H vessels in CED mice and rescued the number and distribution of Osx$^+$, Col1α$^+$, and Ocn$^+$ cells.

In the aberrant bone remodeling, TGF-β stimulates formation of type H vessels in an incorrect temporal and spatial manner to form an abnormal, highly pro-osteogenic microenvironment. TGF-β then recruits LepR$^+$ cells, which undergo osteoblastic differentiation under regulation by the local microenvironment. The aberrant bone formation leads to osteoclast-mediated bone resorption, and the degraded matrix culminated in greater release of TGF-β. The bone targeting conjugate directly inhibits TGF-β signaling in bone, restores the normal pro-osteoblastic microenvironment, decreases migration of BMSCs, and rescues aberrant bone formation in CED mice.

In summary, conjugate Compound 1 can deliver TβR1I specifically to bone. By inhibiting TGF-β signaling, Compound 1 restored normal bone remodeling in CED mice with no obvious side effects. It was also found that elevated TGF-β signaling stimulates migration of LepR$^+$ cells and formation of type H vessels, leading to aberrant bone formation. The results support that the bone-targeting TβR1I conjugate can provide an advantageous alternative treatment for CED and other aberrant bone remodeling diseases, such as Paget's disease and osteopetrosis.

Biological Example 2. Treatment of Osteoarthritis

This Example shows in vitro and in vivo animal model studies of the conjugates of the present disclosure, e.g., Compound 1, in treating osteoarthritis. Animals such as mice, rats for this Example can be obtained from known sources/methods as described in U.S. Publication No. 2015/0139909. ELISA and Western Blot, Histochemistry, Immunohistochemistry and Histomorphometry, Flow cytometry, in vivo micro-MRI, micro-computed tomography, CT-based miocroangiography, gait analysis, and statistics methods for this Example follow the procedures described in U.S. Publication No. 2015/0139909.

Mice. C57BL/6J (wild type) mice can be from Charles River. Two months old male mice are anesthetized with ketamine and xylazine and then the anterior cruciate ligament is transected surgically to induce mechanical instability associated osteoarthritis on the right knee. Sham operations are done on independent mice. For the time-course experiment, operated animals are euthanized at 0, 14, 30, 60 and 90 days post surgery, n=8-12. For the dosage screening experiment, 2-month-old sham and ACLT-operated mice are assigned into 6 groups, n=10 per group. Beginning three days after surgery, different doses (e.g., 0.1, 0.5, 1, 2.5, and 5 mg kg$^{-1}$) of Conjugates (e.g., Compound 1), TGF-beta Inhibitors (e.g., Compound S-3) are injected or the equivalent volume of vehicle (DMSO+PBS) intra-peritoneally daily for 30 days. Mice are euthanized 30 and 60 days post surgery.

CED mice can be generated as previously described, in which the CED-derived TGF-β1 mutation (H222D) is specifically expressed by osteoblastic cells driven by a 2.3-kb type I collagen promoter.

Rats. Two month-old male Lewis rats can be purchased from Charles River. ACLT is conducted as described as above. After ACLT, a canal in the medial plateau is made using a 20G needle. An alginate bead containing 0.1 μg 1D11 (TGF-β1 neutralizing antibody, R&D Systems, Minneapolis, MN) or vehicle is embedded in the subchondral bone canal. The canal is then closed with bone wax. The animals are euthanized at 0, 1, 2, and 3 months post surgery (n=8 per group). Knee joints are processed for μCT and histological analysis accordingly.

Cell Culture. Green fluorescent protein (GFP)-labeled mouse adult MSCs can be obtained from the Texas A&M Health Science Center College of Medicine Institute (College Station). Cells (Passage 3-5) can be maintained in Iscove's modified Dulbecco's medium (Invitrogen) supplemented with 10% fetal calf serum (Atlanta Biologicals), 10% horse serum (Thermo Scientific), and 1% penicillin-streptomycin (Mediatech). MSCs can be cultured in 6-well plates at a density of $1.8 \times 10^5$ cells per well, then are starved for 6 h followed by TGF-β1 (R&D Systems) and TβRI inhibitor (e.g., Compound S-3) or Conjugate (e.g., Compound 1) treatment.

Elevated Active TGF-β and Bone Resorption in Subchondral Bone. The subchondral bone changes at the onset of osteoarthritis were studied in detail in U.S. Publication No. 2105/0139909 by transecting the ACL in mice to generate a destabilized osteoarthritis animal model and analyzed the effects over time. Briefly, the tibial subchondral bone volume in ACLT mice was found to be dramatically changed relative to sham operated controls post surgery in three-dimensional CT analysis. The total subchondral bone tissue volume (TV) increased by more than 20% compared to that of sham controls by 2 months post surgery. The thickness of subchondral bone plate (SBP) fluctuated significantly from 14 to 60 days post surgery with abnormal morphology by 60 days. Moreover, the disruption of connectivity and micro-architecture of trabecular bone was indicated by significantly increased trabecular pattern factor (Tb. Pf) in the ACLT mice compared to that of sham operated controls, indicating uncoupled bone remodeling. Proteoglycan loss in cartilage was observed 30 days post surgery and was further aggravated at 60 days. Proteoglycan loss was detected at the deep zone of articular cartilage. H&E staining showed that thickness of the calcified cartilage zone increased with the tidemark moving closer to articular surface. OARSI scores revealed the degeneration of articular cartilage started by 14 days post ACLT and progressed gradually. TRAP staining showed that the number of osteoclasts increased in the subchondral bone as early as 7 days post surgery, and the continued osteoclastic bone resorption generated large bone marrow cavities by 30 days. Immunostaining demonstrated that post surgery, the number of pSmad2/3$^+$ cells increased by 7 days, maintained at high concentrations until 30 days and then gradually decreased back to baseline by 60 days. It was thus concluded that the results suggested that altered mechanical loading induced subchondral bone resorption with elevated TGF-β concentrations in the subchondral bone.

Subchondral Bone TGF-β Inhibition Attenuates Cartilage Degeneration. This experiment is to examine the effect of Conjugate (e.g., Compound 1) on the prevention of degeneration of articular cartilage during osteoarthritis development. Specifically, the effects of inhibition of TGF-β activity are examined on ACLT joints. TβRI inhibitor (e.g., Compound S-3) and Conjugate (e.g., Compound 1) are injected at different doses with ACLT mice. The effects on subchondral bone structure, proteoglycan loss in articular cartilage, trabeculae connectivity and micro-architecture, normalization of subchondral bone TV, maintenance of the thickness of SBP and volume decrease in Tb. Pf are monitored against control treated groups. Proteoglycan loss and calcification of articular cartilage are attenuated in ACLT mice 2 months post surgery, a time point often used for analysis of destabilized osteoarthritis mice models. The protective effect on articular cartilage in TβRI inhibitor or Conjugate treated compared to vehicle treated ACLT mice is quantified using OARSI system. The effects of the TβRI inhibitor or Conjugate are also determined on the concentrations of MMP13 or type X collagen in chondrocytes as compared to vehicle treated ACLT group.

Similar studies are carried out in 9-month-old ACLT mice. Subchondral bone structure improvement and attenuated articular cartilage degeneration are also monitored in aged ACLT mice treated with TβRI inhibitor or Conjugate. Moreover, gait analysis with Catwalk system is performed to reveal any significant disparity between the percentages of maximum contact time (Maxcontactat %) of the two hind limbs two months post surgery, which is rescued in the inhibitor-treated or Conjugate-treated ACLT group.

It is expected that the Conjugates herein (e.g., Compound 1) can have similar or better efficacy compared to the TβRI inhibitor tested in U.S. Publication No. 2015/0139909.

Increase of MSC Clusters Leads to Osteoid Islets in the Subchondral Bone Marrow. As detailed in U.S. Publication No. 2015/0139909, nestin$^+$ MSCs (mesenchymal stem cells) in subchondral bone marrow were dramatically increased in numbers by 30 days post surgery in ACLT mice as compared to that of sham controls, which effect can be prevented by TORI inhibitor. Similarly, osterix$^+$ osteoprogenitors were largely located on the bone surface in sham controls and the significantly increased number of osteoprogenitor clusters detected in the bone marrow in the vehicle-treated ACLT group was attenuated with TβRI inhibitor treatment. Osteocalcin$^+$ osteoblasts and osteoids as islets were observed in the marrow of the ACLT subchondral bone and the abnormal localization of the osteoid islets was also found to be reduced by injection of TβRI inhibitor. Lastly, U.S. Publication No. 2015/0139909 shows that the formation of osteoid islets were reduced by the TβRI inhibitor compared to the vehicle-treated group in fluorescent double labeling experiment.

Similar to the experiment described in U.S. Publication No. 2015/0139909, the effect of injection of the Conjugates herein (e.g., Compound 1) is assessed to show its capability in reducing the nestin$^+$ MSCs in subchondral bone marrow, the abnormal localization of the osteoid islets, and the formation of osteoid islets. Further, the effect of the Conjugates herein (e.g., Compound 1) on Smads (e.g., Smad2/3) are also examined.

The effect of the Conjugates herein (e.g., Compound 1) is also assessed on the level of CD31$^+$ endothelial progenitors, which were previously shown to be significantly increased in the subchondral bone of ACLT mice relative to sham controls, and was reduced by injection of TβRI inhibitor; angiogenesis, and bone marrow lesion in tibial subchondral bone by micro-MRI.

It is expected that the Conjugates herein (e.g., Compound 1) can have similar or better efficacy compared to the TβRI inhibitor tested in U.S. Publication No. 2015/0139909.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

With respect to aspects of the invention described as a genus, all individual species are individually considered separate aspects of the invention. If aspects of the invention are described as "comprising" a feature, embodiments also are contemplated "consisting of" or "consisting essentially of" the feature.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference. To the extent that any meaning or definition of a term in this document conflicts with any meaning or definition of the same term in a document incorporated by reference, the meaning or definition assigned to that term in this document shall govern.

What is claimed is:

1. A compound of Formula I, a pharmaceutically acceptable ester thereof, a zwitterion thereof, or a pharmaceutically acceptable salt thereof,

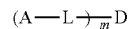

Formula I wherein:
A at each occurrence is independently

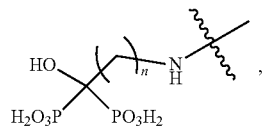

wherein n is an integer of 1-10;
L is
(i) a carbonyl group, which joins A and D via

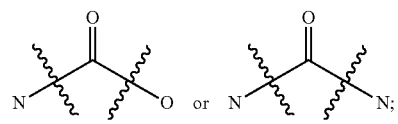

(ii) null, and A and D are joined via an amide bond; or
(iii) a Formula III,

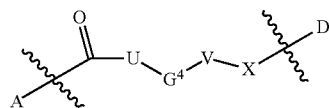

Formula III wherein
U and V are each independently —O—, —O-G$^5$-, —NH—, —NH-G$^6$-, —N(C$_{1-6}$ alkyl)-, —N(C$_{1-6}$ alkyl)-G$^7$-, an optionally substituted alkylene, an optionally substituted heteroalkylene, optionally substituted cycloalkylene, optionally substituted heterocyclylene, optionally substituted arylene, optionally substituted heteroarylene, or null;
G$^4$, G$^5$, G$^6$, and G$^7$ are each independently an optionally substituted alkylene, an optionally substituted heteroalkylene, optionally substituted cycloalkylene, optionally substituted heterocyclylene, optionally substituted arylene, optionally substituted heteroarylene, or null; and
X is C(=O) or null;
m is 1; and
D is characterized as having a Formula IIf:

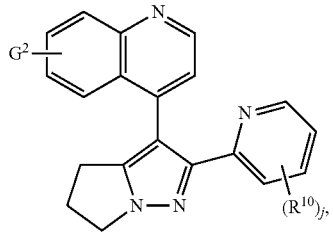

Formula IIf wherein R[10] at each occurrence is independently halogen, hydroxyl, an optionally substituted $C_{1-4}$ alkyl, or an optionally substituted $C_{1-4}$ alkoxy; and j is an integer of 0-3;

wherein:

$G^2$ is

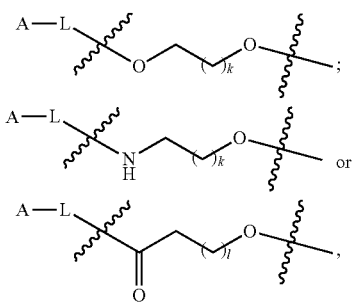

wherein each k is independently an integer of 1-6, and l is an integer of 0-6.

2. The compound of claim 1, a pharmaceutically acceptable ester thereof, a zwitterion thereof, or a pharmaceutically acceptable salt thereof, wherein D is selected from Formulae IIg, IIh, and IIi:

Formula IIg

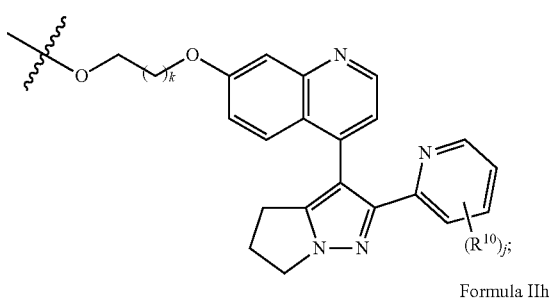

Formula IIh

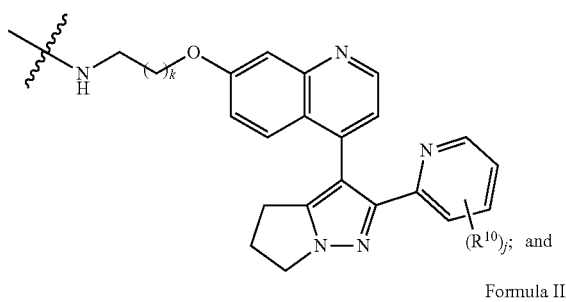

Formula IIi

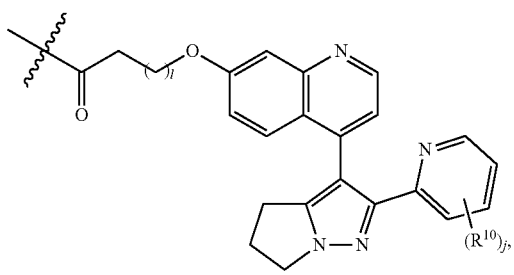

wherein each k is 1 or 2, and l is 0, 1, or 2.

3. The compound of claim 1, a pharmaceutically acceptable ester thereof, a zwitterion thereof, or a pharmaceutically acceptable salt thereof, wherein L is a carbonyl group, which joins A and D via

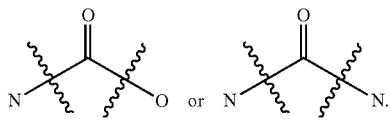

4. The compound of claim 1, a pharmaceutically acceptable ester thereof, a zwitterion thereof, or a pharmaceutically acceptable salt thereof, wherein L is null, and A and D are joined via an amide bond.

5. The compound of claim 1, a pharmaceutically acceptable ester thereof, a zwitterion thereof, or a pharmaceutically acceptable salt thereof, wherein L is

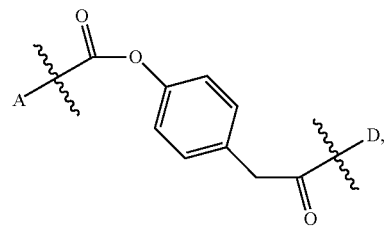

wherein D attaches to L through an oxygen or nitrogen atom.

6. The compound of claim 1, a pharmaceutically acceptable ester thereof, a zwitterion thereof, or a pharmaceutically acceptable salt thereof, wherein A is

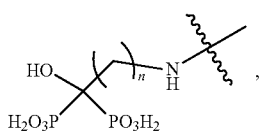

wherein n is 1, 2, or 3.

7. The compound of claim 1, or a pharmaceutically acceptable salt thereof, which is a sodium salt of the compound.

8. A pharmaceutical composition comprising the compound of claim 1, a pharmaceutically acceptable ester thereof, a zwitterion thereof, or a pharmaceutically acceptable salt thereof, and optionally a pharmaceutically acceptable excipient.

9. A method of ameliorating a bone disease or disorder associated with aberrant TGFβ activities in a subject in need thereof, the method comprising administering to the subject the compound of claim 1, a pharmaceutically acceptable ester thereof, a zwitterion thereof, or a pharmaceutically acceptable salt thereof, or a pharmaceutical composition comprising the compound of claim 1, a pharmaceutically acceptable ester thereof, a zwitterion thereof, or a pharmaceutically acceptable salt thereof.

10. The method of claim 9, wherein the administering is via an oral route, injection, infusion, or inhalation.

11. The method of claim 9, wherein the bone disease or disorder is osteoarthritis.

12. A method of ameliorating osteoarthritis, fibrosis, cancer metastasis, or Camurati-Engelmann disease in a subject in need thereof, the method comprising administering to the subject a therapeutically effective amount of the compound of claim 1, a pharmaceutically acceptable ester thereof, a zwitterion thereof, or a pharmaceutically acceptable salt thereof, or a pharmaceutical composition comprising the compound of claim 1, a pharmaceutically acceptable ester thereof, a zwitterion thereof, or a pharmaceutically acceptable salt thereof.

13. The method of claim 12, wherein the administering is via an oral route, injection, infusion, or inhalation.

14. A method of ameliorating osteoarthritis in a subject in need thereof, the method comprising administering to the subject a therapeutically effective amount of the compound of claim 1, a pharmaceutically acceptable ester thereof, a zwitterion thereof, or a pharmaceutically acceptable salt thereof, or a pharmaceutical composition comprising the compound of claim 1, a pharmaceutically acceptable ester thereof, a zwitterion thereof, or a pharmaceutically acceptable salt thereof.

15. The method of claim 14, wherein the administering is via an oral route, injection, infusion, or inhalation.

16. A compound, a pharmaceutically acceptable ester thereof, a zwitterion thereof, or a pharmaceutically acceptable salt thereof, wherein the compound is selected from:

(Compound 1)

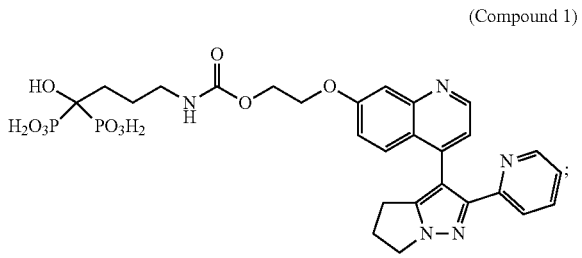

(Compound 2)

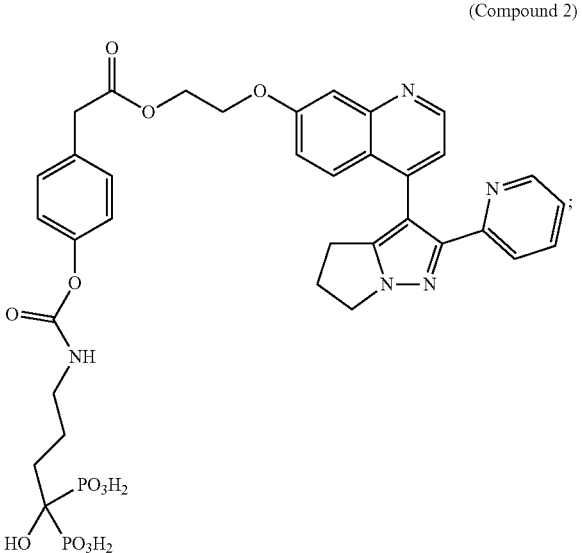

(Compound 3)

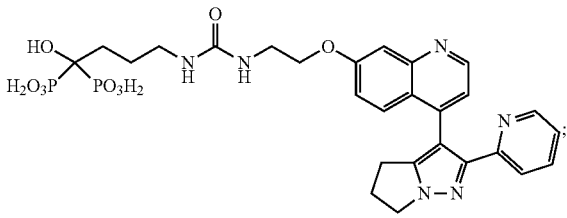

(Compound 4)

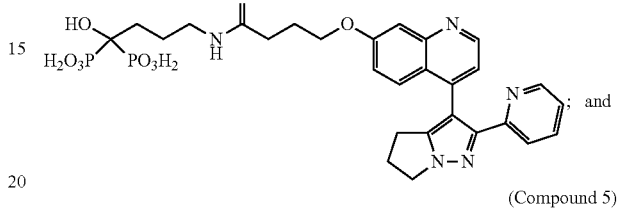

(Compound 5)

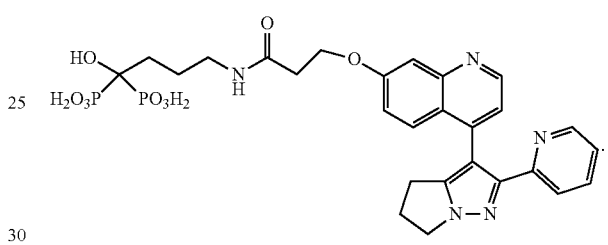

17. The compound of claim 16, or a pharmaceutically acceptable salt thereof, which is a sodium salt of the compound.

18. A method of ameliorating a bone disease or disorder associated with aberrant TGFβ activities in a subject in need thereof, the method comprising administering to the subject the compound of claim 16, a pharmaceutically acceptable ester thereof, a zwitterion thereof, or a pharmaceutically acceptable salt thereof, or a pharmaceutical composition comprising the compound of claim 16, a pharmaceutically acceptable ester thereof, a zwitterion thereof, or a pharmaceutically acceptable salt thereof.

19. A method of ameliorating osteoarthritis, fibrosis, cancer metastasis, or Camurati-Engelmann disease in a subject in need thereof, the method comprising administering to the subject a therapeutically effective amount of the compound of claim 16, a pharmaceutically acceptable ester thereof, a zwitterion thereof, or a pharmaceutically acceptable salt thereof, or a pharmaceutical composition comprising the compound of claim 16, a pharmaceutically acceptable ester thereof, a zwitterion thereof, or a pharmaceutically acceptable salt thereof.

20. A method of ameliorating osteoarthritis in a subject in need thereof, the method comprising administering to the subject a therapeutically effective amount of the compound of claim 16, a pharmaceutically acceptable ester thereof, a zwitterion thereof, or a pharmaceutically acceptable salt thereof, or a pharmaceutical composition comprising the compound of claim 16, a pharmaceutically acceptable ester thereof, a zwitterion thereof, or a pharmaceutically acceptable salt thereof.

21. A compound, a pharmaceutically acceptable ester thereof, a zwitterion thereof, or a pharmaceutically acceptable salt thereof, wherein the compound is Compound 1:

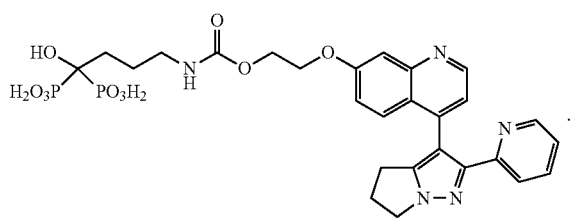
(Compound 1)

22. The compound of claim 21, or a pharmaceutically acceptable salt thereof, which is a sodium salt of Compound 1.

23. A pharmaceutical composition comprising the compound of claim 21, a pharmaceutically acceptable ester thereof, a zwitterion thereof, or a pharmaceutically acceptable salt thereof, and optionally a pharmaceutically acceptable excipient.

24. A method of ameliorating a bone disease or disorder associated with aberrant TGFβ activities in a subject in need thereof, the method comprising administering to the subject the compound of claim 21, a pharmaceutically acceptable ester thereof, a zwitterion thereof, or a pharmaceutically acceptable salt thereof, or a pharmaceutical composition comprising the compound of claim 21, a pharmaceutically acceptable ester thereof, a zwitterion thereof, or a pharmaceutically acceptable salt thereof.

25. A method of ameliorating osteoarthritis, fibrosis, cancer metastasis, or Camurati-Engelmann disease in a subject in need thereof, the method comprising administering to the subject a therapeutically effective amount of the compound of claim 21, a pharmaceutically acceptable ester thereof, a zwitterion thereof, or a pharmaceutically acceptable salt thereof.

26. A method of ameliorating osteoarthritis in a subject in need thereof, the method comprising administering to the subject a therapeutically effective amount of the compound of claim 21, a pharmaceutically acceptable ester thereof, a zwitterion thereof, or a pharmaceutically acceptable salt thereof.

27. The method of claim 26, wherein the administering is via an oral route, injection, infusion, or inhalation.

28. A method of ameliorating osteoarthritis in a subject in need thereof, the method comprising administering to the subject a therapeutically effective amount of a pharmaceutical composition comprising the compound of claim 21, a pharmaceutically acceptable ester thereof, a zwitterion thereof, or a pharmaceutically acceptable salt thereof.

29. A method of ameliorating osteoarthritis in a subject in need thereof, the method comprising administering to the subject a therapeutically effective amount of a sodium salt of the compound of claim 21.

30. A method of ameliorating osteoarthritis in a subject in need thereof, the method comprising administering to the subject a therapeutically effective amount of a pharmaceutical composition comprising a sodium salt of the compound of claim 21.

* * * * *